United States Patent
Radic et al.

(10) Patent No.: US 12,350,296 B2
(45) Date of Patent: Jul. 8, 2025

(54) LIQUID PROPOLIS EXTRACT, ITS FORMULATION AND USE THEREOF

(71) Applicant: Apiotix Technologies D.O.O., Split (HR)

(72) Inventors: Sasa Radic, Split (HR); Bozo Radic, Zagreb (HR); Jelena Suran, Zagreb (HR)

(73) Assignee: Apiotix Technologies D.O.O., Split (HR)

( * ) Notice: Subject to any disclaimer, the term of this patent is extended or adjusted under 35 U.S.C. 154(b) by 922 days.

(21) Appl. No.: 17/430,567

(22) PCT Filed: Feb. 12, 2020

(86) PCT No.: PCT/EP2020/053573
§ 371 (c)(1),
(2) Date: Aug. 12, 2021

(87) PCT Pub. No.: WO2020/169425
PCT Pub. Date: Aug. 27, 2020

(65) Prior Publication Data
US 2022/0133810 A1    May 5, 2022

(30) Foreign Application Priority Data

Feb. 19, 2019   (HR) ............................ P20190325A
Feb. 3, 2020    (HR) ............................ P20200178A

(51) Int. Cl.
| | |
|---|---|
| A61K 35/644 | (2015.01) |
| A23L 21/20 | (2016.01) |
| A61K 8/98 | (2006.01) |
| A61K 9/06 | (2006.01) |
| A61P 31/12 | (2006.01) |
| A61Q 19/00 | (2006.01) |

(52) U.S. Cl.
CPC ............ *A61K 35/644* (2013.01); *A23L 21/20* (2016.08); *A61K 8/988* (2013.01); *A61K 9/06* (2013.01); *A61P 31/12* (2018.01); *A61Q 19/00* (2013.01)

(58) Field of Classification Search
None
See application file for complete search history.

(56) References Cited

U.S. PATENT DOCUMENTS

| | | | |
|---|---|---|---|
| 4,382,886 A | | 5/1983 | Sosnowski |
| 2013/0006011 A1 | | 1/2013 | Ricchiuto et al. |

FOREIGN PATENT DOCUMENTS

| | | |
|---|---|---|
| CN | 1685928 A | 10/2005 |
| CN | 103278575 A | 9/2013 |
| CN | 108181388 A | 6/2018 |
| JP | 2004159563 A | 6/2004 |
| KR | 20130134800 A | 12/2013 |
| WO | WO-2011/092511 A1 | 8/2011 |
| WO | WO-2011/141007 A2 | 11/2011 |
| WO | WO-2014/176654 A1 | 11/2014 |

OTHER PUBLICATIONS

Zhang (CN 103278575 A—English translation), Sep. 4, 2013.*
International Search Report and Written Opinion for PCT/EP2020/053573 (ISA/EP) mailed Jul. 13, 2020 (10 pages).
Huang et al., *Recent Advances in the Chemical composition of Propolis*, Molecules, vol. 19, No. 12, Nov. 26, 2014, pp. 19610-19632, XP055330723.

* cited by examiner

*Primary Examiner* — Susan Hoffman
(74) *Attorney, Agent, or Firm* — Alston & Bird LLP

(57) ABSTRACT

A novel standardized liquid propolis extract and pharmaceutical formulation based on said extract, as well as their manufacturing methods and uses, are provided. The liquid extract is produced by extraction of crude propolis with an extraction solvent based on a mixture of PEG 200-600 (96.5-99.9% w/w) and lecithins (0.1-3.5% w/w). The extract is characterized with standardized content of p-coumaric acid (1), trans-ferulic acid (2), caffeic acid (3), and CAPE (4). It is used as an active ingredient in manufacturing of pharmaceutical, cosmetic, veterinary, agrochemical or functional food products. The pharmaceutical formulation according to the invention consists of 5-95% w/w of the said propolis extract and up to 100% excipients required for preparation of various dosage forms. It is used for treatment of diseases and conditions in humans and animals such as: inflammatory diseases, bacterial and fungal infections, viral, autoimmune and cancer diseases, and for the treatment of burns and wound healing.

12 Claims, 7 Drawing Sheets

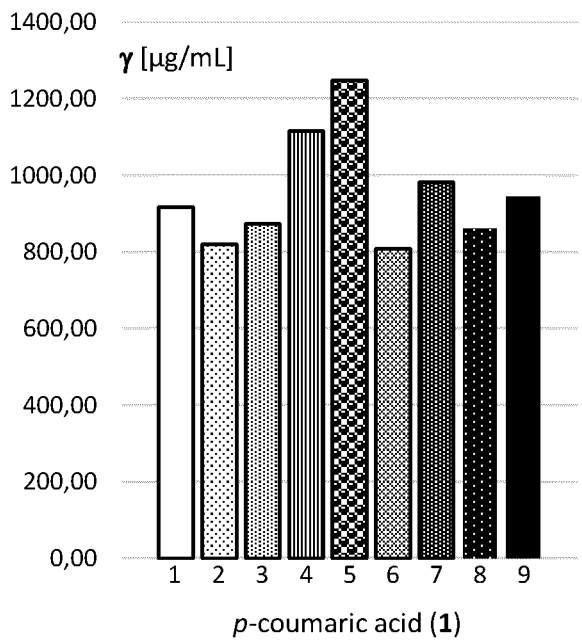

*p*-coumaric acid (1)

Figure 2.1

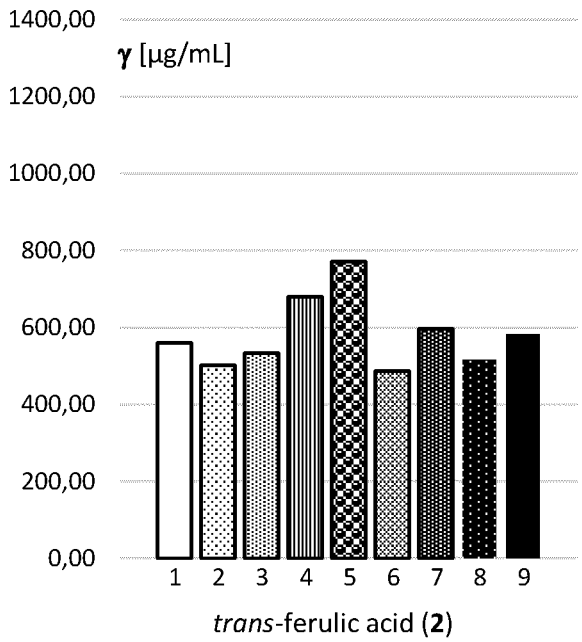

*trans*-ferulic acid (2)

Figure 2.2

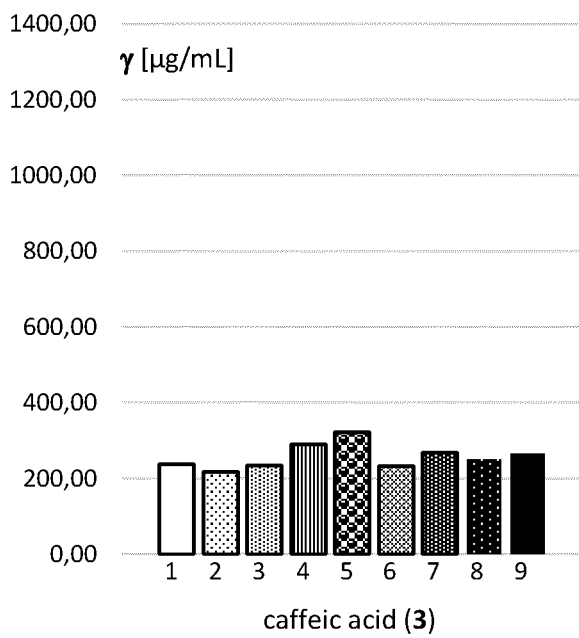

caffeic acid (3)

Figure 2.3

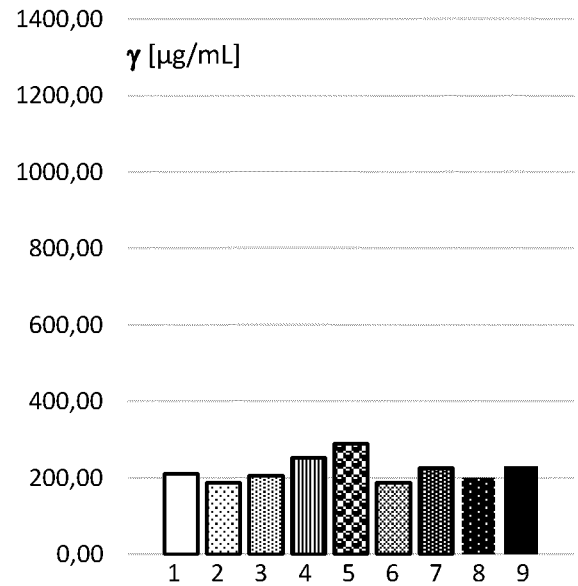

CAPE (4; 2-phenylethyl – 3,4-dihydroxy-*trans*-cinnamate; 2-phenethyl ester of caffeic acid)

Figure 2.4

Extraction solvent for Figures 2.1-2.10
1 – ethanol
2 – ethanol + 3% soybean lecithin (SL)
3 – ethanol + 10% soybean lecithin (SL)
4 – ethanol + 20% soybean lecithin (SL)
5 – ethanol + 30% soybean lecithin (SL)
6 – ethanol + 1.1% rapeseed lecithin (RL)
7 – ethanol + 4% rapeseed lecithin (RL)
8 – ethanol + 2.2 % hydrolysed RL (HRL)
9 – ethanol + 7.7% hydrolysed RL (HRL)

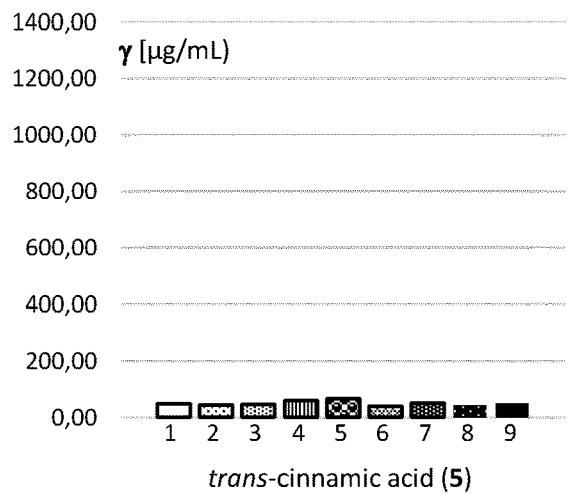
Figure 2.5
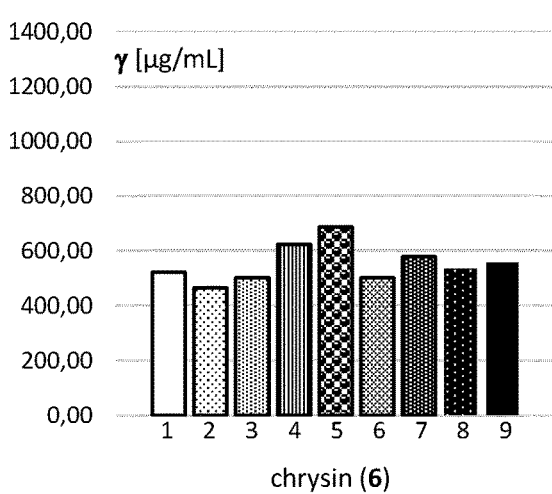
Figure 2.6
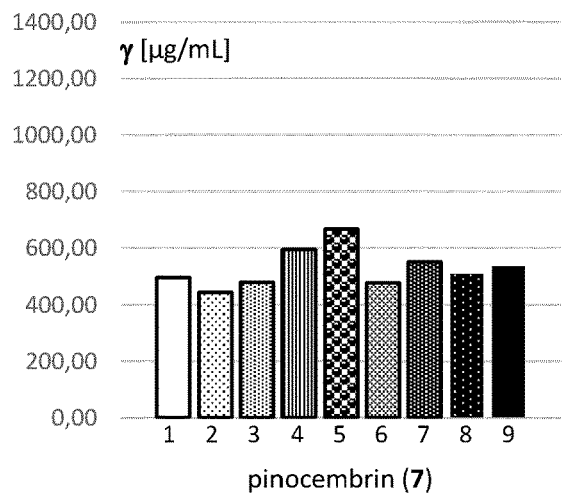
Figure 2.7
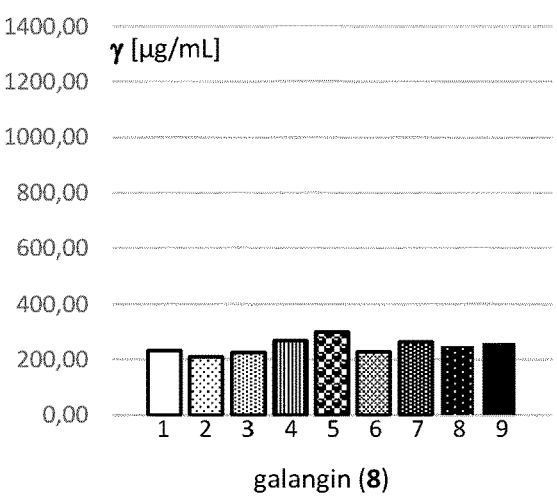
Figure 2.8
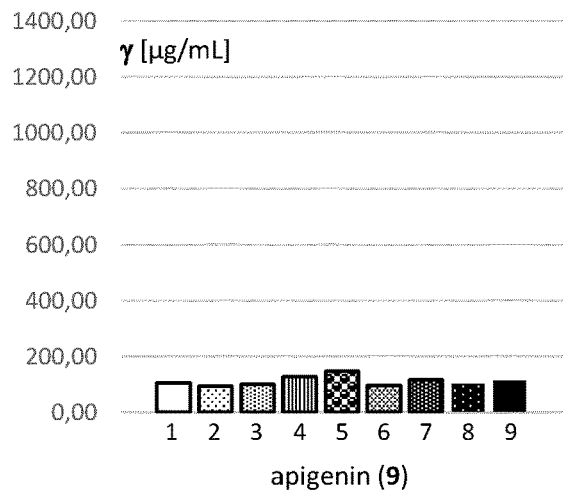
Figure 2.9
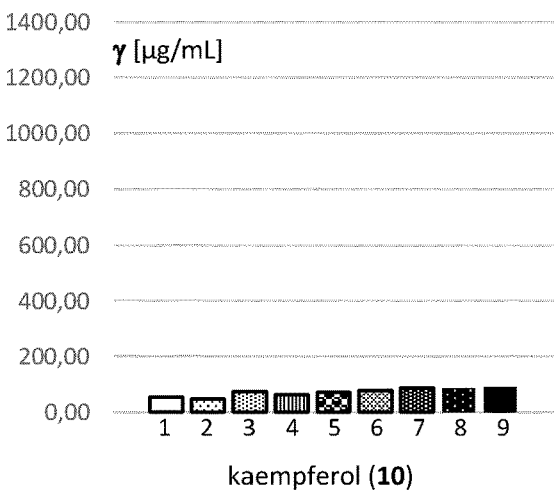
Figure 2.10

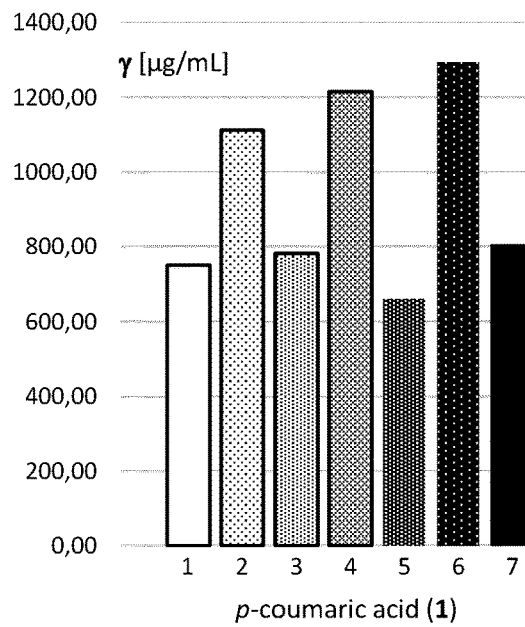
*p*-coumaric acid (1)
Figure 3.1
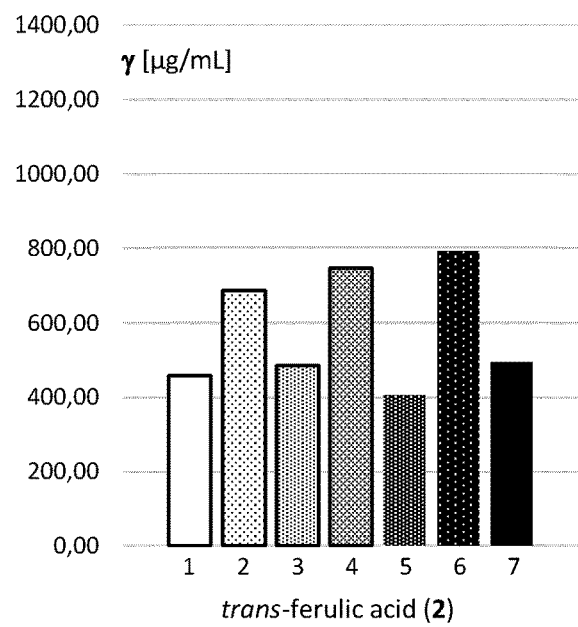
*trans*-ferulic acid (2)
Figure 3.2
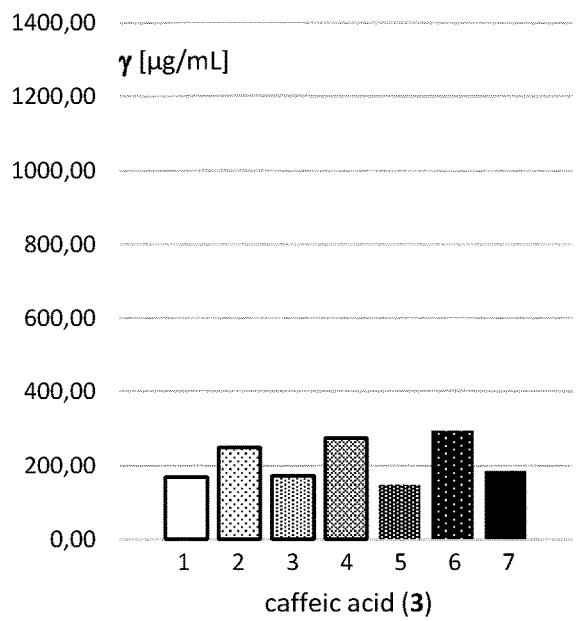
caffeic acid (3)
Figure 3.3
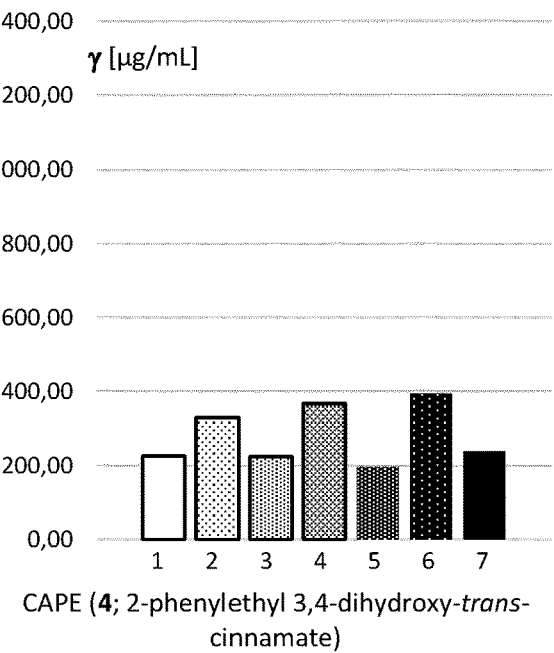
CAPE (4; 2-phenylethyl 3,4-dihydroxy-*trans*-cinnamate)
Figure 3.4
Extraction solvent for Figures 3.1-3.10
1 – PEG 400
2 – PEG 400 + 3% soybean lecithin (SL)
3 – PEG 400 + 10% soybean lecithin (SL)
4 – PEG 400 + 1.1% rapeseed lecithin (RL)
5 – PEG 400 + 4% rapeseed lecithin (RL)
6 – PEG 400 + 2.2% hydrolysed RL (HRL)
7 – PEG 400 + 7.7% hydrolysed RL (HRL)

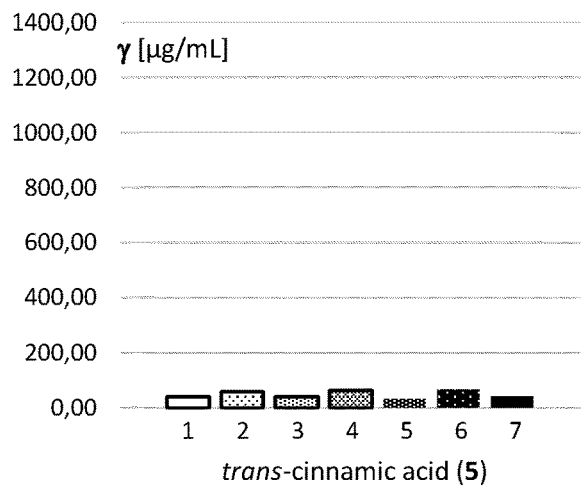
Figure 3.5
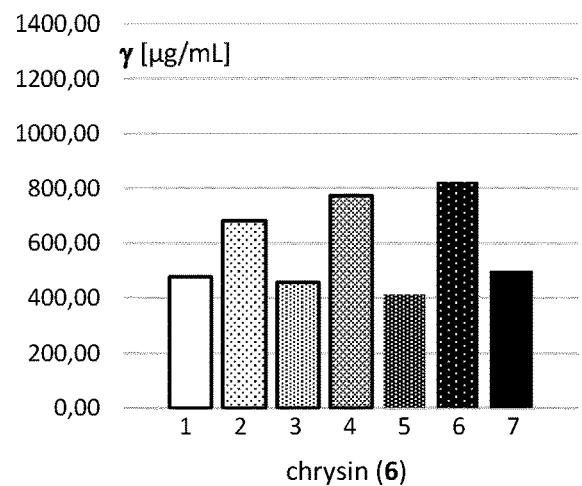
Figure 3.6
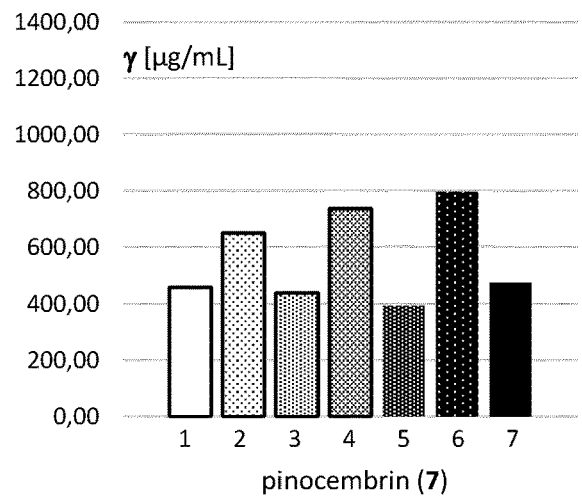
Figure 3.7
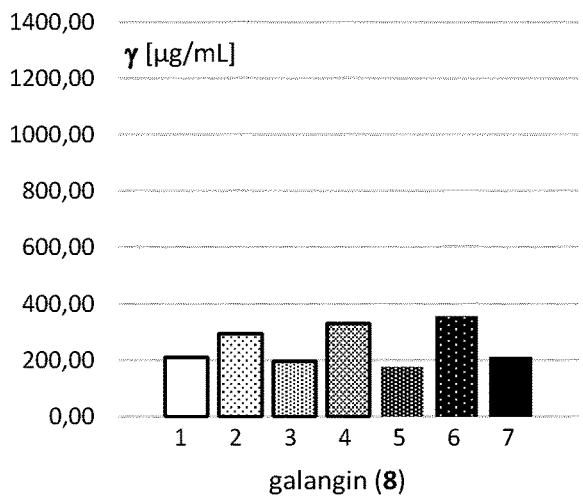
Figure 3.8
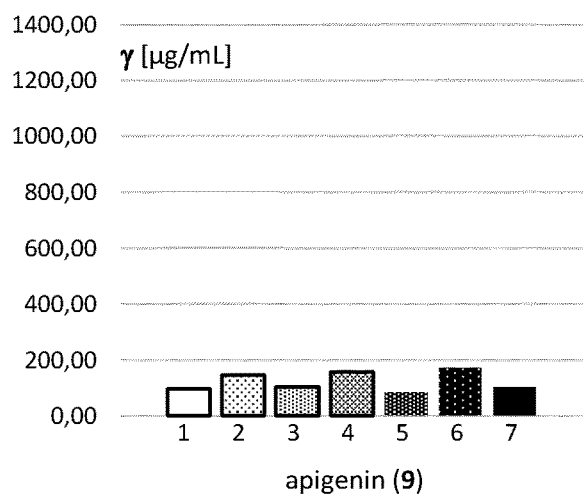
Figure 3.9
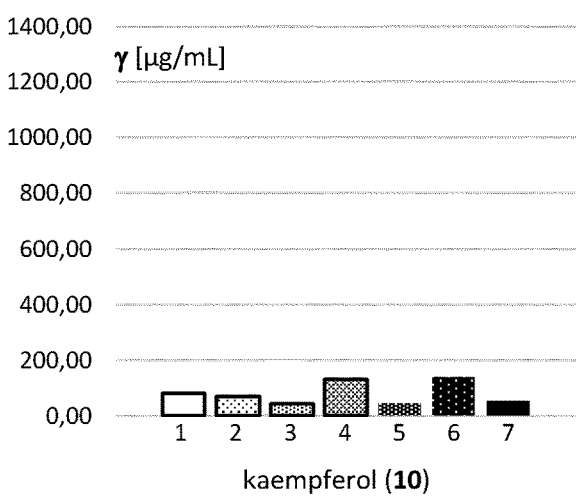
Figure 3.10

LIQUID PROPOLIS EXTRACT, ITS FORMULATION AND USE THEREOF

CROSS-REFERENCE TO RELATED APPLICATIONS

This application is a national phase entry of PCT/EP2020/053573, filed on Feb. 12, 2020, which claims the benefit of priority of Croatian Patent Application No. P20190325A, filed on Feb. 19, 2019, and Croatian Patent Application No. P20200178A, filed on Feb. 3, 2020, the contents of which being hereby incorporated by reference in their entirety for all purposes.

TECHNICAL FIELD

This invention relates to a novel liquid standardized propolis extract, to the process for its preparation to a novel pharmaceutical composition based on the mentioned extract and its use.

BACKGROUND

Propolis is a natural product, harvested by bees which to them, serves as a glue for closing smaller unwanted openings on hives. Propolis contains beeswax as a main ingredient and a large number of various organic compounds. Many of them exhibit significant beneficial pharmacological effects; see for instance literature reference 1:

1) S. Castaldo, F. Capasso: Propolis, and old remedy used in modern medicine, *Fitoterapia* 73 (2002) S1-6.

Beside the mentioned active substances 1-4, propolis contains a whole series of other natural compounds, for example, among acids it contains also trans-cinnamic acid (5), and flavonoid series with a relatively abundant quantity of chrysin (6), pinocembrin (7), galangin (8), apigenin (9) and kaempferol (10):

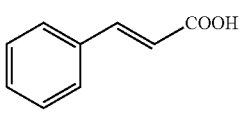

5

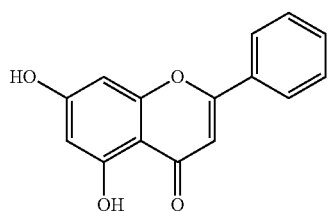

6

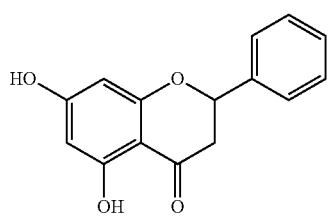

7

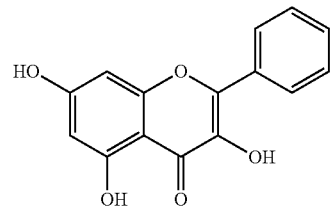

8

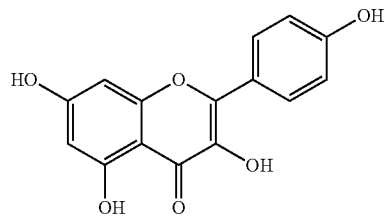

9

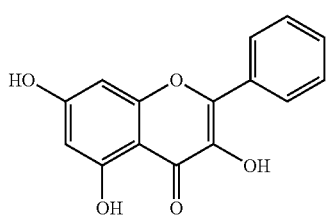

10

Traditionally, crude propolis is extracted with ethanol or mixtures of ethanol and water, yielding so-called propolis tinctures. Such liquid propolis extracts are characterized by several disadvantages:
  (i) the presence of a relatively aggressive solvent (ethanol);
  (ii) alcohol-based products are not suitable for children, pregnant and breastfeeding women and certain patients; and,
  (iii) relatively high content of beeswax, which causes its disaggregation through the phase of mixing with water, during the manufacturing of pharmaceutical and other products, where such an extract is employed as an active ingredient.

Apart from ethanol, as an extraction solvent, glycerol, water, glycerol and water mixtures, and other organic solvents have been used.

In this manner, Tsukada and co-workers disclosed the use of glycerol as an extraction solvent, at the ratio propolis: extraction solvent, 1:2 w/w, at 90-160° C., with subsequent filtration. Such glycerol extracts are water-soluble and suitable for the production of pharmaceutical products as an active pharmaceutical ingredient (API); see literature reference 2:

2) JPH05957A; T. Tsukada, W W. Kameda, M. Ide: Production of water-soluble propolis pharmaceutical preparation; Ogawa Koryo KK, Santapuron KK (JP).

Aqueous propolis extracts are also described in the prior art. The extraction with water as ES can be performed at temperatures from 30-50° C. during 6-8 minutes, which, after filtration, directly gives a liquid propolis extract. The latter can be eventually further processed via microcapsulation through spray-drying technology onto suitable carriers such as maltodextrin and gum arabic into solid extracts; see literature reference 3:

3) CN103783349A; Z. Wang, S. Shao, H. Ma, S. Wang, L. Wang, C. Zhang, X. Ma: Process for preparing honeycomb polyphenol extractive microcapsule by adopting spray; University Jiangsu (CN).

The use of surface-active agents as components of the extraction solvent (ES), which include lecithins, is generally known in the prior art. For example, Paradkar and co-workers described the process for propolis extraction with the use of an aqueous polysorbate solution at 40-90° C. during 2-24 h, yielding a liquid propolis extract; see literature reference 4:

4) WO2011092511A1; A. Paradkar, R. Dhumal, A. Kelly, S. Gilda: Propolis and process for the treatment thereof and end products formed therefrom; Natures Lab Ltd (GB).

Sosnowski disclosed the method for propolis extraction with different organic solvents, including 1,2-propylene glycol, polyethylene glycol (PEG) and mixtures of these solvents with water; see literature reference 5:

5) U.S. Pat. No. 4,382,886; Z. M. Sosnowski: Method for extracting propolis and water soluble dry propolis powder.

Chun and co-workers disclosed the pharmaceutical composition which, among others, is based on a liquid propolis extract in 1,3-butyleneglycol as an extraction solvent, which is, by the use of hydrogenated lecithin, together with other emulsifiers, converted to a pharmaceutical dosage form, which contains nano-particles with this propolis extract; see literature reference 6:

6) KR20130134800A; Y. J. Chun, S. B. Shim, X. Ke: Composition of nano-vesicle containing propolis and manufacturing method of it; University Chungwoon IACF (KR).

Despite the fact that this document does not use lecithin for facilitating extraction of propolis active substances with 1,3-butyleneglycol, certainly it suggests a possibility for its use as a surfactant, which can eventually improve the extraction and emulsifying of certain fatty active propolis ingredients in more polar solvents.

Regarding propolis analytics, there is a large number of analytical methods in the prior art for quantitative determination of propolis active substances in complex propolis extracts, which contain a large number of ingredients. As an example, a similar analytical method to that employed in the present invention, is given in the work of Chinese authors Cui-Ping and co-workers. They described a quantitative method for the determination of 12 different flavonoids and 8 phenolic propolis acids via high performance liquid chromatography (HPLC). This method, among others, enables determination of p-coumaric acid (1), trans-ferulic acid (2) and caffeic acid (3), which are mentioned as qualitative propolis markers; see literature reference 7:

7) Z. Cui-ping, H. Shuai, W. Wen-ting, P. Shun, S. Xiao-ge, L. Ya-jing, H. Fu-liang: Development of high-performance liquid chromatographic for quality and authenticity control of Chinese propolis, *J. Food Sci.* 79 (2014) C1315-C1322.

Due to the content of active substances 1-10 and others, propolis and propolis-extract, exhibit a series of very valuable and beneficial pharmacological effects on human, animal and plant health. There exists a large number of scientific and patent documents in the prior art, that support the wide range of beneficial effects, among which the most significant are as follows: anti-inflammatory; antioxidant; immunomodulatory; hepatoprotective; antimicrobial, including antibacterial, antiviral, antifungal and antiprotozoal; and anticancer; see for instance literature references 8-12:

8) E. L. Ghisalberti: Propolis: A Review, *Bee World* 60 (1979) 59-84.

9) A. Banskota, Y. Tezuka, S. Kadota: Recent Progress in Pharmacological Research of Propolis, *Phytother. Res.* 15 (2001) 561-571.

10) G. A. Burdock: Review of the Biological Properties and Toxicity of Bee Propolis (Propolis), *Food Chem. Toxicol.* 36 (1998) 347-363.

11) J. M. Sforcin: Propolis and the immune system: a review, *J. Ethnopharmacol.* 113 (2007) 1-14.

12) J. W. Dobrowolski, S. B. Vohora, K. Sharma, S. A. Shah, S. A. H. Naqvi, P. C. Dandiya: Antibacterial, antifungal, antiamoebic, antiinflammatory and antipyretic studies on propolis bee products, *J. Ethnopharmacol.* 35 (1991) 77-82.

Beside propolis extracts, a whole range of beneficial pharmacological effects are described in the prior art for certain isolated (pure) propolis active substances, for example:

(i) p-coumaric acid (1); see literature references 13 and 14;

(ii) trans-ferulic acid (2); see literature references 15 and 16;

(iii) caffeic acid (3); see literature references 17 and 18; as well as (iv) 2-phenylethyl 3,4-dihydroxy-trans-cinnamate (4; CAPE); see literature references 19 and 20; which, among other, exhibit immunomodulatory, anti-inflammatory and antimicrobial activities:

13) T. F. Bachiega, C. L. Orsatti, A. C. Pagliarone, J. M. Sforcin: The Effects of Propolis and its Isolated Compounds on Cytokine Production by Murine Macrophages, *Phytother. Res.* 26 (2012) 1308-1313.

14) K. Pei, J. Ou, J. Huang, S. Ou: p-Coumaric acid and its conjugates: dietary sources, pharmacokinetic properties and biological activities, *J. Sci. Food Agric.* 96 (2016) 2956-2962.

15) N. Kumar, V. Pruthi: Potential applications of ferulic acid from natural sources, *Biotechnol. Rep.* 4 (2014) 86-93.

16) C. Shi, X. Zhang, Y. Sun, M. Yang, K. Song, Z. Zheng, Y. Chen, X. Liu, Z. Jia, R. Dong, L. Cui, X. Xia: Antimicrobial activity of ferulic acid against Cronobacter sakazakii and possible mechanism of action, *Foodborne Pathog. Dis.* 13 (2016) 196-204.

17) H. G. Choi, P. T. Tran, J. H. Lee, B. S. Min, J. A. Kim: Anti-inflammatory activity of caffeic acid derivatives isolated from the roots of *Salvia* miltiorrhiza Bunge, *Arch. Pharm. Res.* (2018) 64-70.

18) V. N. Lima, C. D. Oliveira-Tintino, E. S. Santos, L. P. Morais, S. R. Tintino, T. S. Freitas, Y. S. Geraldo, R. L. Pereira, R. P. Cruz, I. R. Menezes, H. D. Coutinho: Antimicrobial and enhancement of the antibiotic activity by phenolic compounds: Gallic acid, caffeic acid and pyrogallol, *Microb. Pathog.* 99 (2016) 56-61.

19) K. Frenkel, H. Wei, R. Bhimani, J. Ye, J. A. Zadunaisky, M.-T. Huang, T. Ferraro, A. H. Conney, D. Grunberger: Inhibition of Tumor Promoter-mediated Processes in mouse Skin and Bovine Lens by Caffeic Acid Phenethyl Ester, *Cancer Res.* 53 (1993) 1255-1261.

20) A. Russo, R. Longo, A. Vanella: Antioxidant activity of propolis: role of caffeic acid phenethyl ester and galangin, *Fitother.* 73 (2002) S21-S29.

Furthermore, propolis active substances are fungicides, bactericides, virucides, insecticides, nematocides and are used in plant protection. Due to a strong antioxidant activity, propolis strengthens plants and enhances their resistance against abiotic stress and helps them to combat infections; see literature references 21-25:

21) C. A. Guginski-Piva, I. dos Santos, A. W. Junior, D. W. Heck, M. F. Flores, K. Pazolini: Propolis for the control of powdery mildew and the induction of phytoalexins in cucumber, *IDESIA* (*Chile*) 33 (2015) 39-47;
22) Z. Ararso, G. Legesse: Insecticidal action of honeybees propolis extract against larvae of lesser wax moth, *Agric. Biol. J. North Am.* (2015) doi:10.5251/abjna.2016.7.6.302.306.
23) L. Kumar, M. K. Mahatma, K. A. Kalariya, S. K. Bishi, A. Mann: Plant Phenolics: Important Bio-Weapon against Pathogens and Insect Herbivores, *Popular Kheti* 2 (2014) 149-152;
24) E. M. Noweer, M. G. Dawood: Efficiency of propolis extract on faba bean plants and its role against nematode infection, *Commun. Agric. Appl. Biol. Sci.* 74 (2009) 593-603;
25) K. Kulbat: The role of phenolic compounds in plant resistance, *Biotechnol. Food Sci.* 80 (2016) 97-108.

According to our best knowledge, the use of a specific extraction solvent (ES) based on liquid polyethylene glycol, containing a low (0.1-3.5% m/m) lecithin content, as an enhancer of propolis extraction chemoselectivity, has not been described in the prior art. The application of such specific ES from this invention, enables the enhancement of chemoselectivity in crude propolis extraction, yielding the corresponding liquid extract with a significantly enhanced content of the respective active substances 1-4.

Also, the use of the mentioned, specific, standardized, liquid propolis extract, as an active pharmaceutical ingredient (API) in the pharmaceutical composition according to the present invention, provides unexpected improvement in a series of different indications for its use; as is described in the detailed description of this invention.

BRIEF SUMMARY

Concerning the fact that propolis is a mixture of beeswax and a large number of natural organic compounds, different extraction processes yield extracts of a very different composition of active substances. With the use of chemoselective extraction solvents (ES), which have an ability for selective extraction of predominantly certain groups of organic compounds, together with the use of suitable analytical methods, it is theoretically possible to achieve a consistent and standardized propolis extract composition.

The technical problem that is solved by the present invention includes:
(i) a non-alcoholic liquid propolis extract, which would be characterized by high and standardized content of phenolic propolis acids, para-coumaric acid (1), trans-ferulic acid (2), caffeic acid (3) and 2-phenylethyl ester of caffeic acid, 2-phenethyl 3,4-dihydroxy-trans-cinnamate (4; CAPE), for which several beneficial pharmacological activities are known, on both human and animal organisms;

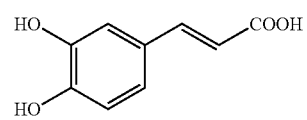

1

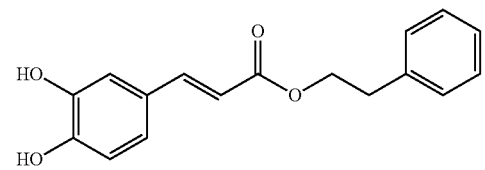

2

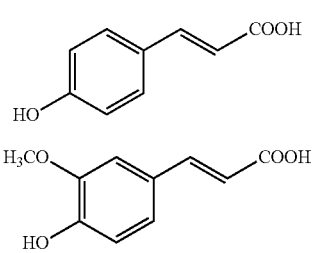

3

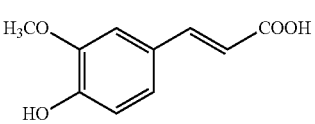

4

(ii) the process for its production;
(iii) use for the production of pharmaceutical, cosmetic, veterinary, agrochemical or food products with known, standardized content of propolis active substances 1-4; and especially,
(iv) a pharmaceutical composition based on the mentioned propolis extract, which would be effective in the treatment of inflammatory and infective diseases, as well as diseases and conditions where the antioxidative, anti-inflammatory and immunomodulatory activity of particular propolis active substances, play an important role in the etiology of their incidence, as suggested by certain references in the state of the art.

Such alcohol-free extracts with negligible beeswax content and other ballast propolis compounds, with high and standardized contents of highly bioactive propolis ingredients, represents a base for the development and production of a highly valuable pharmaceutical, veterinary, agrochemical or functional food products or food supplements. In contrast, the use of standard propolis extracts based on ethanol, glycerol or 1,2-propyleneglycol for this purpose, is coupled with various difficulties such as unknown contents of the above-mentioned propolis active substances or a low quantitative composition of valuable phenolic acids and CAPE against flavonoid propolis ingredients.

The present invention is based on:
(i) the use of a specific extraction solvent (ES) formulation which serves for the chemoselective extraction process of crude propolis;
(ii) a method for quantitative determination of active propolis ingredients including key active substances 1-4;
(iii) standardization of thus prepared liquid propolis extract by dilution with a certain amount of the same extraction solvent, up to the desired level of active substances 1-4 according to this invention; where the said extraction solvent consists of two or more food and pharmaceutically-acceptable substances, and also in the final product, a liquid standardized propolis extract. This same extraction solvent has the role of the carrier or diluent; and,
(iv) the pharmaceutical composition, which is based on the said standardized propolis extract according to this invention, which proved to be an effective agent for treatment of inflammatory and infective diseases. Due to the wide spectra of its pharmacological activity, it can be used for treatment of various diseases and conditions such as: inflammatory diseases, bacterial and fungal infections, viral diseases, autoimmune diseases, for mucosa regeneration, treatment of burns and wounds and for cancer diseases.

The present invention is based on an unexpected efficacy and chemoselectivity of crude propolis extraction with a specific extraction solvent (ES). The latter consists of the mixture of liquid polyethylene glycol (PEG), e.g. PEG 400, and lecithin or hydrolysed lecithin in ratio: 96.5-99.9:0.1-3.5% w/w.

The extraction solvent (ES) effectively and chemoselectively extracts propolis active substances p-coumaric acid (1), trans-ferulic acid (2), caffeic acid (3) and 2-phenethyl 3,4-dihydroxy-trans-cinnamate (4; CAPE). The use of a suitable analytical method, based on high performance liquid chromatography (HPLC), enables a quantitative determination of active substances 1-4 in a such manner prepared primary extract. The latter is subjected to further standardization by dilution with the same ES which was employed in the extraction step, up to the desired content of active substances 1-4 according to the present invention. In this manner, a liquid propolis extract with known and standardized concentrations of key active substances 1-4, according to this invention, is obtained. This is further used as an active pharmaceutical ingredient (API), active cosmetic ingredient (ACI), or as food ingredient for manufacturing of functional food and food supplements.

The composition from this invention based on the said liquid propolis extract, which contains key active substances p-coumaric acid (1; 10-1,300 µg/mL), trans-ferulic acid (2; 10-800 µg/mL), caffeic acid (3; 5-300 µg/mL), and 2-phenethyl 3,4-dihydroxy-trans-cinnamate (4; 5-400 µg/mL) is an effective agent in the therapy of inflammatory diseases, bacterial infections, fungal infections, viral diseases, autoimmune diseases, functional gastrointestinal disorders, for mucosa regeneration, treatment of burns and wounds, as well as in treatment of cancer diseases.

BRIEF DESCRIPTION OF THE SEVERAL VIEWS OF THE DRAWING(S)

FIG. 1 shows a typical HPLC chromatogram of key propolis ingredients 1-4 and accompanied ingredients 5-10.

FIGS. 2.1-2.4 shows the results of quantitative composition of propolis active substances 1-4 in liquid propolis extracts obtained by extraction with ethanol (96%) and mixtures of ethanol with different kinds and concentrations of lecithins.

FIGS. 2.5-2.10 shows the results of quantitative composition of accompanied substances 5-10 in liquid propolis extracts obtained by extraction with ethanol (96%) and mixtures of ethanol with different kinds and concentrations of lecithins.

FIGS. 3.1-3.4 shows the results of quantitative composition of propolis active substances 1-4 in liquid propolis extracts obtained by extraction with polyethylene glycol 400 and mixtures of polyethylene glycol 400 with different kinds and concentrations of lecithins.

FIGS. 3.5-3.10 shows the results of quantitative composition of accompanied substances 5-10 in liquid propolis extracts obtained by extraction with polyethylene glycol 400 and mixtures of polyethylene glycol 400 with different kinds and concentrations of lecithins.

ABBREVIATIONS

Figure 1:
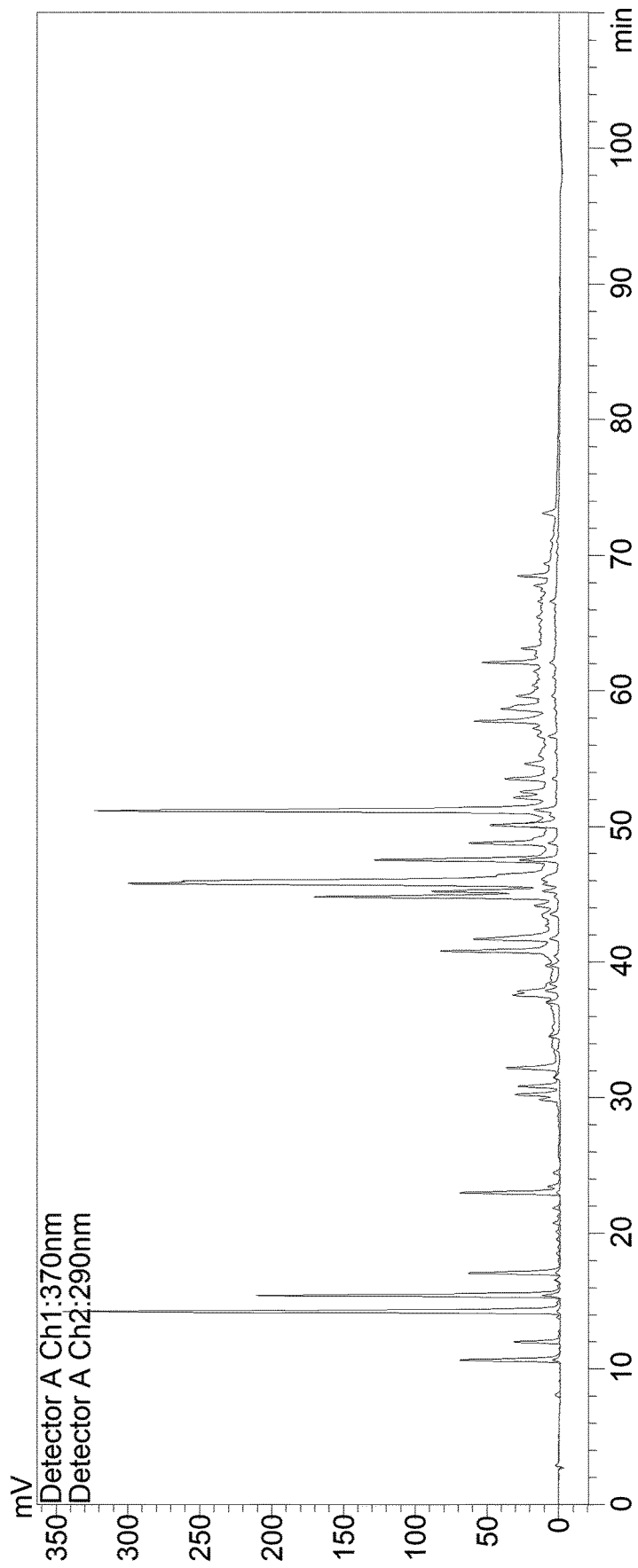
Figure 4:
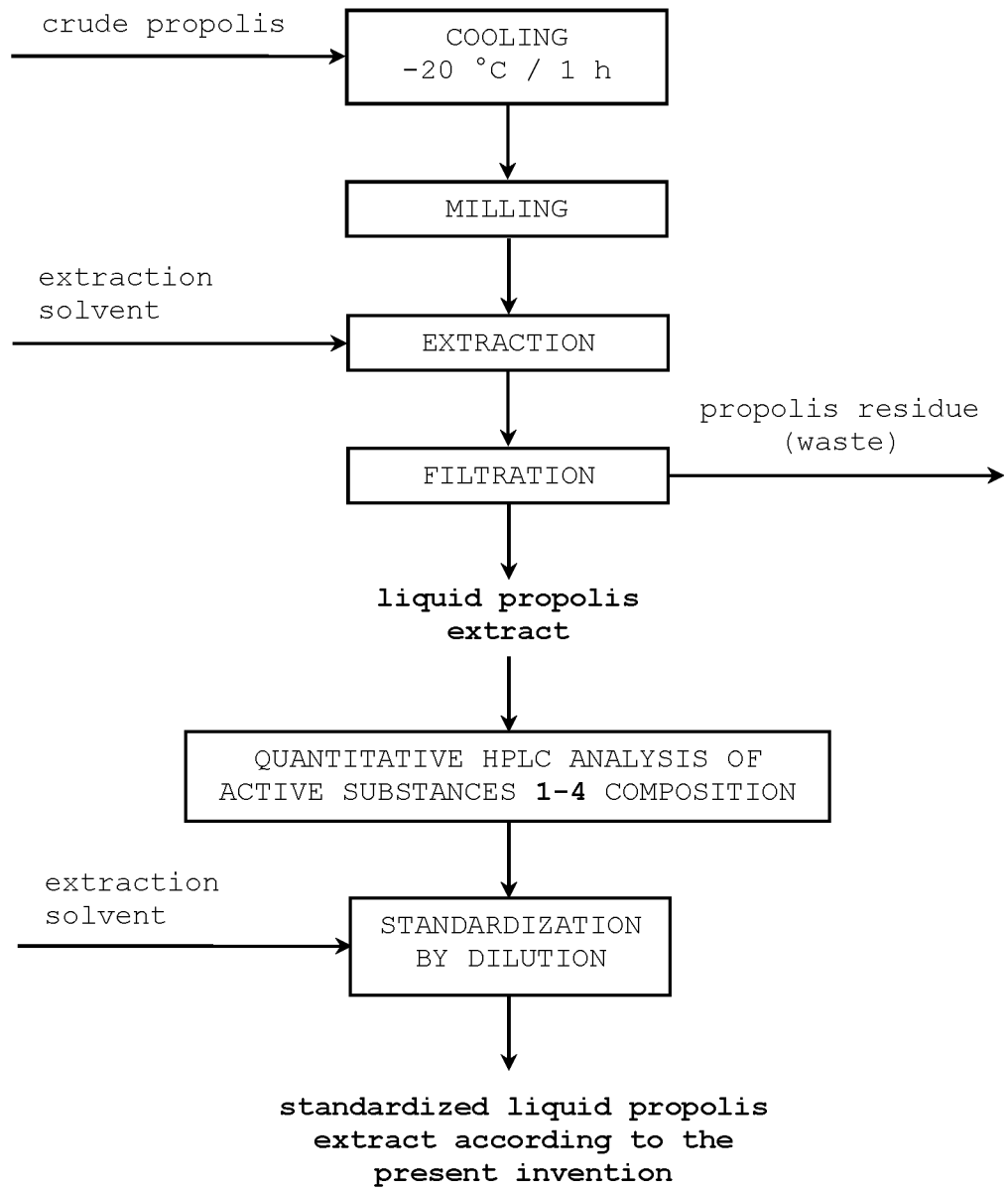
FIG. 4 shows a block scheme of the process for production of a standardized liquid propolis extract according to the present invention.

ES—extraction solvent
SL—soybean lecithin (*Glycine max.* L.)
RL—rapeseed lecithin (*Brassica napus* L.)
HRL—hydrolysed soybean lecithin
SUL—deoiled sunflower lecithin
EtOH—96% ethanol
PEG—polyethylene glycol
HPLC—high performance liquid chromatography
GC—gas chromatography
TLC—thin layer chromatography
MIC—minimal inhibitory concentration
RPMI—Roswell Park Memorial Institute medium
TTC—2,3,5-triphenyl-2H-tetrazolium chloride, redox indicator
PBS—phosphate buffer in saline solution
CFU—colony forming units; number of living microorganisms capable of forming colonies
XTT—XTT sodium salt; 2,3-bis(2-methoxy-4-nitro-5-sulphophenyl)-2H-tetrazolium-5-carboxanilide inner salt, redox indicator
MRSA—methicillin-resistant *Staphylococcus aureus*
MSSA—methicillin-sensitive *Staphylococcus aureus*
CLSI—Clinical and Laboratory Standards Institute
EUCAST—European Committee on Antimicrobial Susceptibility Testing
API—active pharmaceutical ingredient/substance
DER—drug-to-extract, weight ratio; measure of the extracts strength expressed by the weight ratio of a starting drug and a final extract
SCC—somatic cell count
i.mam.—intramammary (application)
ATCC—American Type Culture Collection; non-profit organization which collects, stores, and distributes standard reference microorganisms
CNS—coagulase-negative staphylococci

DETAILED DESCRIPTION

The present invention relates to the novel liquid propolis extract, standardized in the content of the key active substances, selected from the group consisting of: p-coumaric acid (1), trans-ferulic acid (2), caffeic acid (3) and caffeic acid 2-phenylethyl ester, 2-phenethyl 3,4-dihydroxy-trans-cinnamate (4), the process for its preparation and its use.

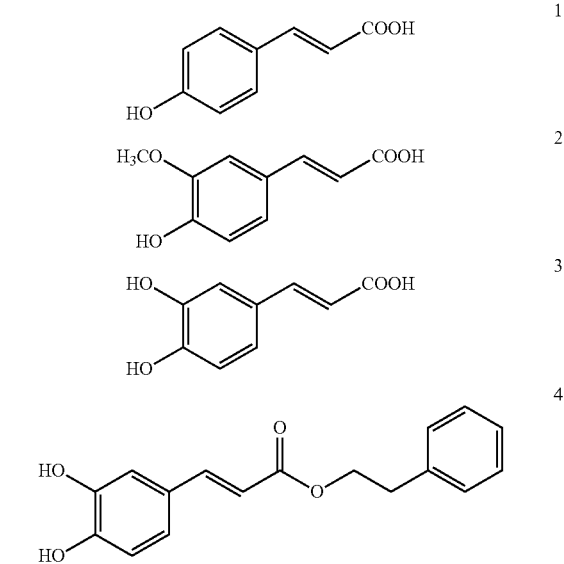

The liquid propolis extract as a pharmaceutical, cosmetic or agrochemical ingredient or food ingredient, according to the present invention consists of:
(A) a dry propolis extract; 0.1-10.0% w/w; and
(B) an extraction solvent; 90.0-99.9% w/w;
where the extraction solvent consists of:
(B.1) one or more liquid polyethylene glycols (PEG) 200-600; 96.5-99.9% w/w; and
(B.2) lecithin or hydrolysed lecithin; 0.1-3.5% w/w;
where the said liquid propolis extract is standardized by:
(I) the quantitative weight ratio of crude propolis as a drug and final extract (DER) in the ratio of:
1: 2-1:20 w/w; and
(II) the quantitative content of propolis active substances, selected from the group consisting of p-coumaric acid (1), trans-ferulic acid (2), caffeic acid (3) and 2-phenylethyl 3,4-dihydroxycinnamate (4), where the quantitative composition of minimally two of four, of the said key active substances are as follows:
(i) p-coumaric acid (1); 100-1,300 μg/mL;
(ii) trans-ferulic acid (2); 75-800 μg/mL;
(iii) caffeic acid (3); 25-300 μg/mL; and
(iv) 2-phenylethyl 3,4-dihydroxy-trans-cinnamate (4; CAPE); 40-400 μg/mL.

In the preferred embodiment of this invention, liquid polyethylene glycol (PEG) as the component of the extraction solvent (ES), is selected from the group consisting of: polyethylene glycol 200, polyethylene glycol 300, polyethylene glycol 400, polyethylene glycol 600, or mixtures of these substances.

Specifically, liquid polyethylene glycol (PEG) as the component of the extraction solvent (ES), is selected from the group consisting of: polyethylene glycol 200, polyethylene glycol 400, or mixtures of these substances.

Furthermore, lecithin or hydrolysed lecithin is selected from the group consisting of the products characterized by the hydrophilic-lipophilic balance (HLB) factor from 2-12, and selected from the group consisting of: soybean lecithin (SL; from *Glycine max.* L.); sunflower lecithin (SUL; from *Helianthus annuus* L.); rapeseed lecithin (RL; from *Brassica napus* L.); canola lecithin (*Brassica rapa* L.); lecithin from chicken (*Gallus gallus domesticus* L.) eggs; deoiled products of said lecithins; hydrogenated lecithins from said sources; hydrolysed lecithins from said sources; enzyme-modified derivatives of said lecithins; or mixtures of these substances.

Specifically, as lecithin in the present invention, native lecithin, deoiled, hydrogenated, hydrolysed or enzyme-modified lecithin from soybean (*Glycine max.* L.), sunflower (*Helianthus annuus* L.), rapeseed (*Brassica napus* L.) or canola (*Brassica rapa* L.); or mixtures of these substances can be employed.

The term "enzyme-modified lecithin", includes hydrolysed lecithin, obtained by enzyme-catalysed hydrolysis of one higher fatty acid moiety with a generation of glycerol-mono-ester of the higher fatty acids with a remaining phosphate and choline group in the molecule. This results in significantly increased HLB factor of such hydrolysed lecithin.

Preferably, as the extraction solvent (ES) for the preparation of the liquid propolis extract, according to the present invention, the mixture of:
(i) polyethylene glycol (PEG) 200, polyethylene glycol 300, polyethylene glycol 400 or their mixtures; from 97-99% w/w; and
(ii) native lecithin, deoiled lecithin or hydrolysed lecithin from soybean (*Glycine max.* L.), sunflower (*Helianthus annuus* L.), rapeseed (*Brassica napus* L.) or canola (*Brassica rapa* L.); or mixtures of these substances; from 1-3% w/w;
can be used.

In the preferred embodiment of this invention, liquid propolis extract according to the invention is standardized on:
(I) a quantitative weight ratio of crude propolis as the drug against the final extract (DER) in a ratio of:
1: 3-1:5 w/w; and
(II) the quantitative composition of propolis active substances selected from the group consisting of p-coumaric acid (1), trans-ferulic acid (2), caffeic acid (3), and 2-phenylethyl 3,4-dihydroxy-cinnamate (4), where minimally two of four, of the said key active substances, correspond to the following quantitative content:
(i) p-coumaric acid (1); 500-1,300 μg/mL;
(ii) trans-ferulic acid (2); 300-800 μg/mL;
(iii) caffeic acid (3); 100-300 μg/mL; and
(iv) 2-phenylethyl 3,4-dihydroxy-cinnamate (4; CAPE); 100-400 μg/mL.

Analytics of Propolis Active Substances in Liquid Extracts

For the development of a novel, standardized, liquid propolis extract according to this invention, the development of a suitable analytical method for the quantitative determination of:
(i) key active propolis substances selected from the group consisting of the above-mentioned: p-coumaric acid (1), trans-ferulic acid (2), caffeic acid (3), and 2-phenylethyl 3,4-dihydroxy-cinnamate (4); and
(ii) accompanied active substances selected from the group consisting of: trans-cinnamic acid (5), chrysin (6), pinocembrin (7), galangin (8), apigenin (9) and kaempferol (10)
was essential.

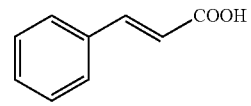

5

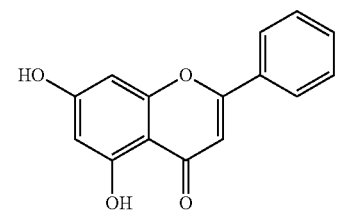

6

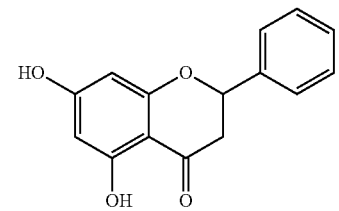

7

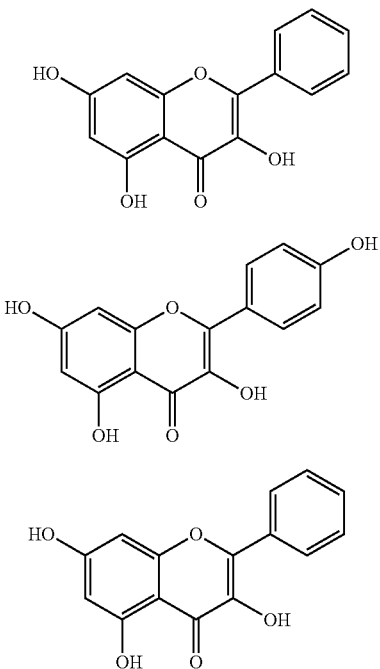

For the purpose of the initial study of the said analytical method, model liquid propolis extracts needed to be prepared. The model propolis extracts in ethanol (96%) and polyethylene glycol were used. These were prepared by the standard extraction method, via maceration at room temperature during 24 h. Then, undissolved residue was separated by filtration and the clear filtrate was employed as a model liquid propolis extract for further study. As the model liquid polyethylene glycol, polyethylene glycol 400 (PEG 400) was used. The procedures for the preparation of the model liquid propolis extracts in classical extraction solvents, ethanol (96%) and polyethylene glycol 400, are described in Example 1 (96% ethanol) and Example 2 (PEG 400).

A suitable analytical method, based on high performance liquid chromatography (HPLC) was developed, by which, a successful separation of all of the 10 said compounds 1-10 was achieved. The method is precisely described in Example 3.

A typical HPLC chromatogram, obtained by the present analytical method is shown in FIG. 1. The retention times ($t_R$) of compounds 1-10 are given in Table 1.

TABLE 1

Retention times of propolis active substances 1-10 according to the HPLC method from the present invention.[a]

| No. | Propolis active substance | Retention time ($t_R$) [min] |
|---|---|---|
| 1 | p-coumaric acid (1) | 14.13 |
| 2 | trans-ferulic acid (2) | 15.31 |
| 3 | caffeic acid (3) | 10.57 |
| 4 | 2-phenylethyl 3,4-dihydroxy-trans-cinnamate (4) | 48.62 |
| 5 | trans-cinnamic acid (5) | 29.76 |
| 6 | chrysin (6) | 44.68 |
| 7 | pinocembrin (7) | 47.39 |

TABLE 1-continued

Retention times of propolis active substances 1-10 according to the HPLC method from the present invention.[a]

| No. | Propolis active substance | Retention time ($t_R$) [min] |
|---|---|---|
| 8 | galangin (8) | 49.94 |
| 9 | apigenin (9) | 37.72 |
| 10 | kaempferol (10) | 36.87 |

[a]Chromatographic column:
Ascentis express; C18;
dimensions:
15 cm × 3.0 mm;
particles in the column:
2.7 μm;
mobile phase:
A = 0.1% formic aqueous solution,
B = methanol;
gradient:
0 min, 80% A, 20% B; 3 min, 70% A, 30% B; 60 min, 20% A, 80% B; 90 min, 20% A, 80% B; 100 min, 70% A, 30% B; 105 min, 80% A, 20% B;
column temperature:
30° C.;
flow:
0.25 mL/min;
analysis time:
110 min;
wavelengh on the UV-VIS detector: for detection:
370 nm, for integration 290 nm;
injection volume:
10 μL;
pressure:
210-190 bars.

Study of Lecithin Influence on Extraction Efficacy of Propolis Active Substances 1-4

In continuation of this research, the effect of different extraction solvents (ES), with content of various kinds (SL, RL, HRL) and concentrations (1-30% w/w) of lecithins, on the efficacy of the propolis active substance 1-4 extraction was studied; see Table 2.

TABLE 2

Extraction solvent (ES) systems tested for extraction of active substances 1-4 from propolis.

| No. | Solvent | Lecithin | Weight ratio solvent:lecithin (w/w) | Experiment |
|---|---|---|---|---|
| 1 | EtOH | — | — | Example 1 |
| 2 | EtOH | SL | 97:3 | Example 4, E1 |
| 3 | EtOH | SL | 90:10 | Example 4, E2 |
| 4 | EtOH | SL | 80:20 | Example 4, E3 |
| 5 | EtOH | SL | 70:30 | Example 4, E4 |
| 6 | EtOH | RL | 98.9:1.1 | Example 4, E5 |
| 7 | EtOH | RL | 96:4 | Example 4, E6 |
| 8 | EtOH | HRL | 97.8:2.2 | Example 4, E7 |
| 9 | EtOH | HRL | 92.3:7.7 | Example 4, E8 |
| 10 | PEG 400 | — | — | Example 2 |
| 11 | PEG 400 | SR | 97:3 | Example 5, E1 |
| 12 | PEG 400 | SR | 90:10 | Example 5, E2 |
| 13 | PEG 400 | RL | 98.9:1.1 | Example 5, E3 |
| 14 | PEG 400 | RL | 96:4 | Example 5, E4 |
| 15 | PEG 400 | HRL | 97.8:2.2 | Example 5, E5 |
| 16 | PEG 400 | HRL | 92.3:7.7 | Example 5, E6 |

EtOH = 96% ethanol;
PEG 400 = polyethylene glycol 400;
SL = soybean lecithin;
RL = rapeseed lecithin;
HRL = hydrolysed rapeseed lecithin.

Thus prepared liquid propolis extracts were subjected to quantitative analysis against the content of key active substances 1-4, and accompanied active substances 5-10. The results are given in Tables 3-6.

In the case of the use of the extraction solvent (ES) based on 96% ethanol (EtOH) and mixtures of EtOH and different kinds (SL, RL, HRL) and concentration (1-30% w/w within ES composition), primary liquid propolis extracts contain p-coumaric acid (1; approx. 800-1250 µg/mL), trans-ferulic acid (2; approx. 485-770 µg/mL), caffeic acid (3; approx. 185-290 µg/mL) and 2-phenylethyl 3,4-dihydroxy-trans-cinnamate (4; CAPE; approx. 215-320 µg/mL) as dominant active ingredients; see Table 3.

TABLE 3

Quantitative composition of active substances 1-4 in liquid propolis extracts obtained with ethanol-based extraction solvents (ES).

| ES | p-coumaric acid (1) γ [µg/mL] (FIG. 2.1) | trans-ferulic acid (2) γ [µg/mL] (FIG. 2.2) | caffeic acid (3) γ [µg/mL] (FIG. 2.3) | 2-phenethyl-3,4-dihydroxy cinnamate (4) γ [µg/mL] (FIG. 2.4) |
|---|---|---|---|---|
| 1 | 916.32 | 559.26 | 209.49 | 236.68 |
| 2 | 820.35 | 501.87 | 186.22 | 216.63 |
| 3 | 872.51 | 533.16 | 204.30 | 232.98 |
| 4 | 1116.27 | 679.58 | 251.24 | 289.45 |
| 5 | 1248.16 | 770.88 | 288.66 | 320.75 |
| 6 | 808.30 | 485.32 | 185.58 | 231.19 |
| 7 | 981.25 | 596.21 | 225.33 | 266.46 |
| 8 | 861.11 | 516.41 | 196.96 | 248.14 |
| 9 | 945.73 | 582.69 | 228.69 | 263.48 |

TABLE 3-continued

Quantitative composition of active substances 1-4 in liquid propolis extracts obtained with ethanol-based extraction solvents (ES).

Extraction solvent (ES)

| | |
|---|---|
| 1 - EtOH | 6 - EtOH + 1.1% RL |
| 2 - EtOH + 3% SL | 7 - EtOH + 4% RL |
| 3 - EtOH + 10% SL | 8 - EtOH + 2.2% HRL |
| 4 - EtOH + 20% SL | 9 - EtOH + 7.7% HRL |
| 5 - EtOH + 30% SL | |

ES = extraction solvent;
EtOH = 96% ethanol;
SL = soybean lecithin;
RL = rapeseed lecithin;
HRL = hydrolysed rapeseed lecithin.

Herein the concentration of auxiliary active substances 5-10 were at the following level: trans-cinnamic acid (5; approx. 40-65 µg/mL), chrysin (6; approx. 500-690 µg/mL), pinocembrin (7; approx. 440-670 µg/mL), galangin (8; approx. 210-300 µg/mL), apigenin (9; approx. 90-150 µg/mL) and kaempferol (10; approx. 45-90 µg/mL); see Table 4.

In the case of the use of the extraction solvent (ES) based on polyethylene glycol (PEG 400) and mixtures of PEG 400 and various kinds (SL, RL, HRL) and concentrations (1-10% w/w within ES composition) of lecithins, primary liquid extracts also contain p-coumaric acid (1; approx. 750-1300 µg/mL), trans-ferulic acid (2; approx. 400-800 µg/mL), caffeic acid (3; approx. 140-300 µg/mL) and 2-phenylethyl 3,4-dihydroxy-trans-cinnamate (4; CAPE; approx. 190-370 µg/mL); see Table 5.

TABLE 4

Quantitative composition of accompanied active substances 5-10 in liquid propolis extracts obtained with ethanol-based extraction solvents (ES).

| ES | trans-cinnamic acid (5) γ[µg/mL] | chrysin (6) γ[µg/mL] | pinocembrin (7) γ[µg/mL] | galangin (8) γ[µg/mL] | apigenin (9) γ[µg/mL] | kaempferol (10) γ[µg/mL] |
|---|---|---|---|---|---|---|
| 1 | 48.88 | 521.03 | 496.38 | 232.36 | 103.38 | 54.00 |
| 2 | 43.06 | 463.66 | 444.22 | 208.74 | 93.41 | 47.72 |
| 3 | 46.60 | 499.97 | 479.67 | 224.56 | 100.84 | 74.08 |
| 4 | 58.37 | 623.32 | 594.05 | 267.18 | 127.17 | 62.16 |
| 5 | 65.92 | 685.81 | 665.44 | 297.85 | 146.91 | 71.11 |
| 6 | 40.53 | 500.50 | 477.17 | 226.86 | 96.11 | 79.10 |
| 7 | 51.21 | 576.39 | 552.12 | 263.99 | 115.45 | 87.40 |
| 8 | 43.15 | 534.08 | 510.26 | 245.27 | 102.79 | 85.78 |
| 9 | 51.21 | 557.42 | 535.33 | 256.51 | 111.98 | 88.93 |

Extraction solvent (ES)

1 - EtOH
2 - EtOH + 3% SL
3 - EtOH + 10% SL
4 - EtOH + 20% SL
5 - EtOH + 30% SL
6 - EtOH + 1.1% RL
7 - EtOH + 4% RL
8 - EtOH + 2.2% HRL
9 - EtOH + 7.7% HRL

ES = extraction solvent;
EtOH = 96% ethanol;
SL = soybean lecithin;
RL = rapeseed lecithin;
HRL = hydrolysed rapeseed lecithin.

TABLE 5

Quantitative composition of active substances 1-4 in liquid propolis extracts obtained with polyethylene glycol 400-based extraction solvents (ES).

| EO | p-coumaric acid (1) γ [μg/mL] (FIG. 3.1) | trans-ferulic acid (2) γ [μg/mL] (FIG. 3.2) | caffeic acid (3) γ [μg/mL] (FIG. 3.3) | 2-phenethyl-3,4-dihydroxy cinnamate (4) γ [μg/mL] (FIG. 3.4) |
|---|---|---|---|---|
| 1 | 750.57 | 458.93 | 167.79 | 226.14 |
| 2 | 1112.08 | 685.14 | 249.67 | 329.41 |
| 3 | 781.98 | 485.75 | 171.88 | 223.99 |
| 4 | 1215.61 | 745.35 | 274.49 | 366.41 |
| 5 | 659.80 | 405.60 | 146.30 | 194.79 |
| 6 | 1294.35 | 792.50 | 292.18 | 392.23 |
| 7 | 806.44 | 495.64 | 182.80 | 236.48 |

Extraction solvent (ES)

1 - PEG 400
2 - PEG 400 + 3% SL
3 - PEG 400 + 10% SL
4 - PEG 400 + 1.1% RL
5 - PEG 400 + 4% RL
6 - PEG 400 + 2.2% HRL
7 - PEG 400 + 7.7% HRL

ES = extraction solvent;
PEG 400 = polyethyleneglycol 400;
SL = soybean lecithin;
RL = rapeseed lecithin;
HRL = hydrolysed rapeseed lecithin.

In this case the concentration of auxiliary active substances 5-10 were at the level: trans-cinnamic acid (5; approx. 30-70 μg/mL), chrysin (6; approx. 400-830 μg/mL), pinocembrin (7; approx. 390-800 μg/mL), galangin (8; approx. 190-360 μg/mL), apigenin (9; approx. 80-170 μg/mL) and kaempferol (10; approx. 40-140 μg/mL); see Table 6.

TABLE 6

Quantitative composition of accompanied active substances 5-10 in liquid propolis extracts obtained with polyethylene glycol 400-based extraction solvents (ES).

| ES | trans-cinnamic acid (5) γ[μg/mL] | chrysin (6) γ[μg/mL] | pinocembrin (7) γ[μg/mL] | galangin (8) γ[μg/mL] | apigenin (9) γ[μg/mL] | kaempferol (10) γ[μg/mL] |
|---|---|---|---|---|---|---|
| 1 | 38.40 | 476.77 | 457.71 | 208.31 | 97.03 | 80.18 |
| 2 | 57.81 | 681.36 | 649.38 | 293.11 | 145.59 | 68.23 |
| 3 | 39.28 | 456.61 | 437.36 | 196.76 | 103.89 | 43.00 |
| 4 | 62.14 | 772.55 | 736.93 | 329.80 | 157.13 | 130.60 |
| 5 | 32.92 | 412.97 | 391.23 | 172.80 | 84.25 | 44.46 |
| 6 | 66.58 | 824.77 | 794.67 | 354.62 | 171.29 | 138.94 |
| 7 | 40.75 | 499.97 | 473.43 | 210.09 | 103.22 | 54.16 |

Extraction solvent (ES)

1 - PEG 400
2 - PEG 400 + 3% SL
3 - PEG 400 + 10% SL
4 - PEG 400 + 1.1% RL
5 - PEG 400 + 4% RL
6 - PEG 400 + 2.2% HRL
7 - PEG 400 + 7.7% HRL

ES = extraction solvent;
PEG 400 = polyethylene glycol 400;
SL = soybean lecithin;
RL = rapeseed lecithin;
HRL = hydrolysed rapeseed lecithin.

As can be seen from the results, all tested lecithins (SL, RL, HRL) in combination with any pure solvent, 96% ethanol or polyethylene glycol 400 (PEG 400) when used at lower concentrations, from 1-3% w/w, within the extraction solvent (ES) composition, significantly contribute to the increase of extraction chemoselectivity of active substances 1-4 in comparison to pure solvents.

An unexpected effect of PEG 400 and lecithin (SL, RL, HRL) combination, is revealed in the fact that, while PEG 400 as a pure solvent, extracts active substances 1-4 significantly weaker than 96% ethanol does (Table 3; line 1, column 2); when employed in combination with lecithins (SL, RL, HRL) in concentration from 1-3% w/w, it extracts compounds 1-4 in a significantly more effective manner in comparison to analogous combinations of 96% ethanol with the same lecithins. For instance, although the achieved p-coumaric acid (1) concentration in the extract obtained with 100% PEG 400 as the extraction solvent, was in range 750 μg/mL (Table 5; line 1, column 2) and with 96% EtOH as ES in range 916 μg/mL (Table 3; line 1, column 2), the use of 3% w/w SL in PEG 400 resulted in a concentration of 1.112 μg/mL (Table 5; line 2, column 2), against the level of 820 μg/mL (Table 3; line 2, column 2) in the case of ES use based on 96% ethanol with 3% w/w SL.

From this typical example, a completely unexpected effect of the combination of polyethylene glycol and lecithin in concentration from 1-3% w/w within the extraction solvent (ES) is clearly visible. This can be extrapolated by the person skilled in the art, up to an acceptable range of optimal lecithin weight percentage from 0.1-3.5% w/w within the ES composition.

At the use of higher weight percentages of lecithin within the extraction solvent (ES) composition, the lecithin beneficial effect on propolis extraction chemoselectivity is lost, in comparison to analogous systems based on ethanol. For instance, by employing lecithins in concentrations from 4% RL, 7.7% HRL or 10% SL in ES, lower concentrations of the key active substances 1-4 were recorded, in comparison to the use of analogous ethanol-based ES systems. Typical results are shown in Tables 7 and 8 for two most abundant active substances, p-coumaric acid (1) and trans-ferulic acid (2).

TABLE 7

Quantitative composition of p-coumaric acid (1) in liquid propolis extracts obtained with different extraction solvents according to the present invention.

| ES | p-coumaric acid (1) γ [µg/mL] | Percent change at PEG 400 ES system in comparison to EtOH-based ES (%) [a] | Percent change at EtOH ES system in comparison to PEG 400-based ES (%) [b] |
|---|---|---|---|
| 1 | 916.32 | — | +22.1 |
| 2 | 750.57 | −18.1 | — |
| 3 | 820.35 | — | −26.2 |
| 4 | 1112.08 | +35.6 | — |
| 5 | 872.51 | — | +11.6 |
| 6 | 781.98 | −10.4 | — |
| 7 | 808.30 | — | −33.5 |
| 8 | 1215.61 | +50.4 | — |
| 9 | 981.25 | — | +48.7 |
| 10 | 659.80 | −32.8 | — |
| 11 | 861.11 | — | −33.5 |
| 12 | 1294.35 | +50.3 | — |
| 13 | 945.73 | — | +17.3 |
| 14 | 806.44 | −14.7 | — |

Extraction solvent (ES)

1 - EtOH
2 - PEG 400
3 - EtOH + 3% SL
4 - PEG 400 + 3% SL
5 - EtOH + 10% SL
6 - PEG 400 + 10% SL
7 - EtOH + 1.1% RL
8 - PEG 400 + 1.1% RL
9 - EtOH + 4% RL
10 - PEG 400 + 4% RL
11 - EtOH + 2.2% HRL
12 - PEG 400 + 2.2% HRL
13 - EtOH + 7.7% HRL
14 - PEG 400 + 7.7% HRL

ES = extraction solvent;
EtOH = 96% ethanol;
PEG 400 = polyethylene glycol 400;
SL = soybean lecithin;
RL = rapeseed lecithin;
HRL = hydrolysed rapeseed lecithin.
[a] Increase or decrease percentage (%) of p-coumaric acid (1) concentration in extract obtained with PEG 400-based ES in comparison to analogous ethanol-based ES.
[b] Increase or decrease percentage (%) of p-coumaric acid (1) concentration in extract obtained with ethanol-based ES in comparison to analogous PEG 400-based ES.

In Table 7 one can see the typical unexpected result of the present invention in line 8, column 3, wherein a 50% increase of p-coumaric acid (1) concentration was observed, when the extraction solvent (ES), PEG 400+RL (98.9:1.1, w/w) was used, in comparison to analogous EtOH-based ES (EtOH+RL=98.9:1.1, w/w).

TABLE 8

Quantitative composition of trans-ferulic acid (2) in liquid propolis extracts obtained with different extraction solvents according to the present invention.

| ES | trans-ferulic acid (2) γ [µg/mL] | Percent change at PEG 400 ES system in comparison to EtOH-based ES (%) [a] | Percent change at EtOH ES system in comparison to PEG 400-based ES (%) [b] |
|---|---|---|---|
| 1 | 559.26 | — | +21.9 |
| 2 | 458.93 | −17.9 | — |
| 3 | 501.87 | — | −26.7 |
| 4 | 685.14 | +36.5 | — |
| 5 | 533.16 | — | +9.8 |
| 6 | 485.75 | −10.4 | — |
| 7 | 485.32 | — | −33.5 |
| 8 | 745.35 | +50.4 | — |
| 9 | 596.21 | — | −19.3 |
| 10 | 405.60 | +23.9 | — |
| 11 | 516.41 | — | −34.8 |
| 12 | 792.50 | +53.5 | — |
| 13 | 582.69 | — | +17.6 |
| 14 | 495.64 | −14.9 | — |

Extraction solvent (ES)

1 - EtOH
2 - PEG 400
3 - EtOH + 3% SL
4 - PEG 400 + 3% SL
5 - EtOH + 10% SL
6 - PEG 400 + 10% SL
7 - EtOH + 1.1% RL
8 - PEG 400 + 1.1% RL
9 - EtOH + 4% RL
10 - PEG 400 + 4% RL
11 - EtOH + 2.2% HRL
12 - PEG 400 + 2.2% HRL
13 - EtOH + 7.7% HRL
14 - PEG 400 + 7.7% HRL

ES = extraction solvent;
EtOH = 96% ethanol;
PEG 400 = polyethylene glycol 400;
SL = soybean lecithin;
RL = rapeseed lecithin;
HRL = hydrolysed rapeseed lecithin.
[a] Increase or decrease percentage (%) of trans-ferulic acid (2) concentration in extract obtained with PEG 400-based ES in comparison to analogous ethanol-based ES.
[b] Increase or decrease percentage (%) of trans-ferulic acid (2) concentration in extract obtained with ethanol-based ES in comparison to analogous PEG 400-based ES.

As further typical example of the unexpected result, herein is the data in Table 8, line 12, column 3, where a 53.5% increase in trans-ferulic acid (2) concentration was recorded, when the extraction solvent (ES) PEG 400+HRL (97.8:2.2, w/w) was employed, in comparison to analogous 96% ethanol-based ES.

The process of production of standardized liquid propolis extract according to the present invention The process for production of liquid propolis extract according to the invention includes the following steps:

(i) cooling of crude propolis at −20° C. for minimally 1 h;
(ii) milling of chilled propolis with sieving through 1-8 mm pores;
(iii) extraction of crude propolis with the extraction solvent under the following conditions:
  (a) weight ratio of crude propolis and extraction solvent=1:2-1:20 w/w;
  (b) extraction temperature from 10-150° C.; and
  (c) extraction time from 5 minutes to 72 h;
(iv) filtration of thus obtained mixture through a series of filters with pores from 100 µm to 5 µm, with generation of undissolved residue and the liquid propolis extract;
(v) quantitative analysis of key active propolis substances 1-4 via high performance liquid chromatography (HPLC); and
(vi) standardization of thus obtained liquid propolis extract with determined exact quantitative composition of key active substances 1-4 in the step (v), through dilution with a fresh extraction solvent that has been used in the step (iii), up to the desired content of active substances 1-4.

In the preferred embodiment of the realization of the process for preparation of the liquid propolis extract according to the invention, the extraction step (iii) is performed under the following conditions:

(a) weight ratio of crude propolis and extraction solvent=1:3-1:5 w/w;
(b) extraction temperature from 15-70° C.; and
(c) extraction time from 1-24 h.

Also, the quantitative determination step of key active substances 1-4, and for accompanied monitoring of auxiliary active substances 5-10, the analytical high-performance liquid chromatographic method (HPLC), developed for this purpose, is carried out as follows:
  (i) chromatographic column: Ascentis express; C18; dimensions: 15 cm×3.0 mm; diameter of particles in the column: 2.7 μm;
  (ii) mobile phase: A=0.1% formic acid aqueous solution, B=methanol; gradient: 0 min, 80% A, 20% B; 3 min, 70% A, 30% B; 60 min, 20% A, 80% B; 90 min, 20% A, 80% B; 100 min, 70% A, 30% B; 105 min, 80% A, 20% B;
  (iii) column temperature: 30° C.;
  (iv) flow: 0.25 mL/min;
  (v) analysis time: 110 min;
  (vi) wavelength on UV-VIS detector: for detection: 370 nm, for integration: 290 nm;
  (vii) injection volume: 10 μL;
  (viii) pressure: 210-290 bars.

The experimental procedures for the preparation of liquid propolis extract according to the present invention are disclosed in Examples 4-9. In Example 9, an optimized version of the preparation process for the standardized liquid extract of strength, expressed by the parameter drug-to-extract ratio (DER) weight percentage 1:2, according to the invention, is described.

The analytical method for quantitative determination of the key active substances 1-4 and auxiliary active substances 5-10 is described in Example 3.

Determination of Antimicrobial Efficacy of the Standardized Liquid Extract According to the Present Invention. Determination of Minimal Inhibitory Concentration (MIC) on the Model Pathogenic Microorganisms Antimicrobial efficacy of the propolis extracts was measured at the Department for Molecular medicine of Rudjer Boskovic Institute, Zagreb, Croatia. The minimal inhibitory concentrations (MIC) of standardized liquid propolis extract, according to the present invention, were determined by the directions of CLSI (Clinical and Laboratory Standards Institute) and EUCAST (European Committee on Antimicrobial Susceptibility Testing) methods, as described in literature references 26-29. The product from Example 9 was used.

26) M. Balouiri, M. Sadiki, S. K. Ibnsouda: Methods for in vitro evaluating antimicrobial activity: A review, *J. Pharm. Anal.* 6 (2016) 71-79.
27) CLSI, Methods for Dilution Antimicrobial Susceptibility Tests for Bacteria that Grow Aerobically, Approved Standard, 9th ed., CLSI document M07-A9. Clinical and Laboratory Standards Institute, 950 West Valley Road, Suite 2500, Wayne, Pennsylvania 19087, USA, 2012.
28) CLSI, Reference Reference Method for Broth Dilution Antifungal Susceptibility Testing of Yeasts, Approved Standard, 2nd ed., NCCLS document M27-A2. CLSI, 940 West Valley Road, Suite 1400, Wayne, Pennsylvania 19087-1898, USA, 2002.
29) CLSI, Methods for Determining Bactericidal Activity of Antimicrobial Agents. Approved Guideline, CLSI document M26-A. Clinical and Laboratory Standards Institute, 950 West Valley Road, Suite 2500, Wayne, Pennsylvania 19087, USA, 1998.

Antimicrobial efficacy was tested under in vitro conditions on ATCC strains of the following model pathogenic microorganisms (M):
  (i) *Staphylococcus aureus* ATCC 29293 (M1);
  (ii) methicillin-resistant *Staphylococcus aureus*; MRSA (MFBF collection; M2);
  (iii) methicillin-sensitive *Staphylococcus aureus*; MSSA (MFBF collection; M3);
  (iv) *Enterococcus faecalis* ATCC 9212 (M4);
  (v) *Enterococcus faecalis* VRE (MFBF collection) (M5);
  (vi) *Escherichia coli* ATCC 10536 (146);
  (vii) *Acinetobacter baumanii* ATCC 43498 (M7);
  (viii) *Pseudomonas aeruginosa* ATCC 9027 (M8); and
  (ix) *Candida albicans* ATCC 90028 (149).

A serial microdilution procedure was conducted in order to determine minimal inhibitory concentrations (MIC) of the extracts. The MIC values were determined as the propolis extract concentration at which 80% reduction in bacteria or fungi count occurred ($MIC_{80}$). Minimal inhibitory concentrations ($MIC_{80}$) showed in Table 9, are shown in the form of dilution (%) of the corresponding liquid extract in a given solvent. The starting liquid propolis extract was obtained at the ratio of the crude propolis and the final extract (DER) 1:2; product from Example 9. If the dilution of the liquid extract is larger, meaning that the concentration of active substances 1-10 is lower for MIC, the resulted antimicrobial effect of the tested extract is higher.

Detailed description of the experimental procedure for MIC determination is disclosed in Example 10, and the results are given in Table 9.

TABLE 9

Results of minimal inhibitory concentration (MIC; %) determination of diluted propolis extracts, product from Example 9, in comparison to liquid extracts obtained with 96% ethanol (Example 1) or polyethylene glycol 400 (Example 2) as extraction solvents.

| | | $MIC_{80}$ (%) [a] | | |
|---|---|---|---|---|
| No. | Model microorganism | Liquid extract based on ES1[b] | Liquid extract based on ES2[c] | Liquid extract based on ES3[d] |
| 1 | *Staphylococcus aureus* ATCC 29293 (M1) | 40 | 10 | 40 |
| 2 | MRSA (M2) | 20 | 10 | 40 |
| 3 | MSSA (M3) | 52.5 | 10 | 51.5 |
| 4 | *Enterococcus faecalis* ATCC 9212 (M4) | 10 | 5 | 10 |
| 5 | *Enterococcus faecalis* VRE (M5) | 0 | 0 | 2.5 |
| 6 | *Escherichia coli* ATCC 10536 (M6) | 10 | 10.85 | 12.8 |
| 7 | *Acinetobacter baumanii* ATCC 43498 (M7) | 20 | 10 | 20 |
| 8 | *Pseudomonas aeruginosa* ATCC 9027 (M8) | 0 | 0 | 1.85 |
| 9 | *Candida albicans* ATCC 90028 (M9) | 0 | 0 | 12.85 |

ES = extraction solvent;
ES1 = 96% ethanol;
ES2 = polyethylene glycol 400 (PEG 400);
ES3 = mixture of PEG 400 + 3% soybean lecithin
[a] $MIC_{80}$ is minimal inhibitory concentration of tested substance at which the concentration of living model microorganisms is decreased by 80%. When $MIC_{80}$ = 0, the extract exhibits no effect.
[b] Product from Example 1.
[c] Product from Example 2.
[d] Product from Example 9.

In Tables 10-15, mass concentrations of active substances 1-10 in effective dilutions of the propolis extracts in each of the three tested extraction solvent systems are given; these are obtained by the use of:
  (i) 96% ethanol; product from Example 1,
  (ii) polyethylene glycol 400 (PEG 400); product from Example 2; and,
  (iii) PEG 400 (97% w/w) and soybean lecithin (3% w/w) mixture; product from Example 9;
or, the mass concentrations of corresponding active substances 1-10 at which each particular liquid extract reached MIC. It was determined from the primary liquid extract where DER is 1:2, divided with dilution at which the MIC is achieved.

TABLE 10

Mass concentration (γ) in [µg/mL] for propolis active substances 1-4 in effective dilutions of the liquid propolis extract obtained with 96% ethanol; product from Example 1.

| Model microorganism | Active substance 1-4 | | | |
|---|---|---|---|---|
| | 1 | 2 | 3 | 4 |
| M1 | 22.91 | 13.98 | 5.24 | 5.92 |
| M2 | 45.82 | 27.96 | 10.47 | 11.83 |
| M3 | 17.41 | 10.63 | 3.98 | 4.50 |
| M4 | 90.91 | 55.48 | 20.78 | 23.48 |
| M5 | 916.32 | 559.26 | 209.49 | 236.68 |
| M6 | 91.63 | 55.93 | 20.95 | 23.67 |
| M7 | 45.82 | 27.96 | 10.47 | 11.83 |
| M8 | 916.32 | 559.26 | 209.49 | 236.68 |
| M9 | 916.32 | 559.26 | 209.49 | 236.68 |

Active substance:
para-coumaric acid (1),
trans-ferulic acid (2),
caffeic acid (3),
2-phenylethyl 3,4-dihydroxy-trans-cinnamate (4)
Model microorganism:
S. aureus ATCC 29293 (M1),
MRSA (M2),
MSSA (M3),
E. faecalis ATCC 9212 (M4),
E. faecalis VRE (M5),
E. coli ATCC 10536 (M6),
A. baumanii ATCC 43498 (M7),
P. aeruginosa ATCC 9027 (M8),
C. albicans ATCC 90028 (M9)

TABLE 11

Mass concentration (γ) in [µg/mL] for propolis active substances 5-10 in effective dilutions of the liquid propolis extract obtained with 96% ethanol; product from Example 1.

| Model microorganism | Active substance 5-10 | | | | | |
|---|---|---|---|---|---|---|
| | 5 | 6 | 7 | 8 | 9 | 10 |
| M1 | 1.22 | 13.03 | 12.41 | 5.81 | 2.59 | 1.35 |
| M2 | 2.44 | 26.05 | 24.82 | 11.62 | 5.17 | 2.70 |
| M3 | 0.93 | 9.90 | 9.43 | 4.42 | 1.96 | 1.03 |
| M4 | 4.85 | 51.69 | 49.24 | 23.05 | 10.26 | 5.36 |
| M5 | 48.88 | 521.03 | 496.38 | 232.36 | 103.38 | 54.00 |
| M6 | 4.89 | 52.10 | 49.64 | 23.24 | 10.34 | 5.40 |
| M7 | 2.44 | 26.05 | 24.82 | 11.62 | 5.17 | 2.70 |
| M8 | 48.88 | 521.03 | 496.38 | 232.36 | 103.38 | 54.00 |
| M9 | 48.88 | 521.03 | 496.38 | 232.36 | 103.38 | 54.00 |

Active substance:
cinnamic acid (5),
chrysin (6),
pinocembrin (7),
galangin (8),
apigenin (9),
kaempferol (10)
Model microorganism:
S. aureus ATCC 29293 (M1),
MRSA (M2),
MSSA (M3),
E. faecalis ATCC 9212 (M4),
E. faecalis VRE (M5),
E. coli ATCC 10536 (M6),
A. baumanii ATCC 43498 (M7),
P. aeruginosa ATCC 9027 (M8),
C. albicans ATCC 90028 (M9)

TABLE 12

Mass concentration (γ) in [µg/mL] for propolis active substances 1-4 in effective dilutions of the liquid propolis extract obtained with polyethylene glycol 400 (PEG 400); product from Example 2.

| Model microorganism | Active substance 1-4 | | | |
|---|---|---|---|---|
| | 1 | 2 | 3 | 4 |
| M1 | 75.06 | 45.89 | 16.78 | 22.61 |
| M2 | 75.06 | 45.89 | 16.78 | 22.61 |
| M3 | 75.06 | 45.89 | 16.78 | 22.61 |
| M4 | 433.08 | 264.80 | 96.81 | 130.63 |
| M5 | 750.57 | 458.93 | 167.79 | 226.14 |
| M6 | 69.05 | 42.22 | 15.44 | 20.81 |
| M7 | 75.06 | 45.89 | 16.78 | 22.61 |
| M8 | >750.57 | >458.93 | >167.79 | >226.14 |
| M9 | >750.57 | >458.93 | >167.79 | >226.14 |

Active substance:
para-coumaric acid (1),
trans-ferulic acid (2),
caffeic acid (3),
2-phenylethyl 3,4-dihydroxy-trans-cinnamate (4)
Model microorganism:
S. aureus ATCC 29293 (M1),
MRSA (M2),
MSSA (M3),
E. faecalis ATCC 9212 (M4),
E. faecalis VRE (M5),
E. coli ATCC 10536 (M6),
A. baumanii ATCC 43498 (M7),
P. aeruginosa ATCC 9027 (M8),
C. albicans ATCC 90028 (M9)

TABLE 13

Mass concentration (γ) in [µg/mL] for propolis active substances 5-10 in effective dilutions of the liquid propolis extract obtained with polyethylene glycol 400 (PEG 400); product from Example 2.

| Model microorganism | Active substance 5-10 | | | | | |
|---|---|---|---|---|---|---|
| | 5 | 6 | 7 | 8 | 9 | 10 |
| M1 | 3.84 | 47.68 | 45.77 | 20.83 | 9.70 | 8.02 |
| M2 | 3.84 | 47.68 | 45.77 | 20.83 | 9.70 | 8.02 |
| M3 | 3.84 | 47.68 | 45.77 | 20.83 | 9.70 | 8.02 |
| M4 | 22.16 | 275.10 | 264.10 | 120.20 | 56.05 | 46.26 |
| M5 | 38.40 | 476.77 | 457.71 | 208.31 | 97.03 | 80.18 |
| M6 | 3.53 | 43.86 | 42.11 | 19.17 | 8.93 | 7.38 |
| M7 | 3.84 | 47.68 | 45.77 | 20.83 | 9.70 | 8.02 |
| M8 | >38.40 | >476.77 | >457.71 | >208.31 | >97.03 | >80.18 |
| M9 | >38.40 | >476.77 | >457.71 | >208.31 | >97.03 | >80.18 |

Active substance:
cinnamic acid (5),
chrysin (6),
pinocembrin (7),
galangin (8),
apigenin (9),
kaempferol (10)
Model microorganism:
S. aureus ATCC 29293 (M1),
MRSA (M2),
MSSA (M3),
E. faecalis ATCC 9212 (M4),
E. faecalis VRE (M5),
E. coli ATCC 10536 (M6),
A. baumanii ATCC 43498 (M7),
P. aeruginosa ATCC 9027 (M8),
C. albicans ATCC 90028 (M9)

TABLE 14

Mass concentration (γ) in [µg/mL] for propolis active substances 1-4 in effective dilutions of the liquid propolis extract obtained with the mixture of polyethylene glycol 400 (PEG 400; 97% w/w) and soybean lecithin (3% w/w); product from Example 9.

| Model | Active substance 1-4 | | | |
|---|---|---|---|---|
| microorganism | 1 | 2 | 3 | 4 |
| M1 | 27.80 | 17.13 | 6.24 | 8.24 |
| M2 | 27.80 | 17.13 | 6.24 | 8.24 |
| M3 | 27.80 | 17.13 | 6.24 | 8.24 |
| M4 | 111.21 | 68.51 | 25.00 | 32.94 |
| M5 | 547.05 | 337.03 | 122.82 | 162.05 |
| M6 | 86.50 | 53.29 | 19.42 | 25.62 |
| M7 | 55.60 | 34.26 | 12.48 | 16.47 |
| M8 | 603.22 | 371.64 | 135.42 | 178.68 |
| M9 | 864.95 | 532.89 | 194.19 | 256.21 |

Active substance:
para-coumaric acid (1),
trans-ferulic acid (2),
caffeic acid (3),
2-phenylethyl 3,4-dihydroxy-trans-cinnamate (4)
Model microorganism:
S. aureus ATCC 29293 (M1),
MRSA (M2),
MSSA (M3),
E. faecalis ATCC 9212 (M4),
E. faecalis VRE (M5),
E. coli ATCC 10536 (M6),
A. baumanii ATCC 43498 (M7),
P. aeruginosa ATCC 9027 (M8),
C. albicans ATCC 90028 (M9)

TABLE 15

Mass concentration (γ) in [µg/mL] for propolis active substances 5-10 in effective dilutions of the liquid propolis extract obtained with the mixture of polyethylene glycol 400 (PEG 400; 97% w/w) and soybean lecithin (3% w/w); product from Example 9.

| Model | Active substance 5-10 | | | | | |
|---|---|---|---|---|---|---|
| microorganism | 5 | 6 | 7 | 8 | 9 | 10 |
| M1 | 1.45 | 17.03 | 16.24 | 7.33 | 3.64 | 1.71 |
| M2 | 1.45 | 17.03 | 16.24 | 7.33 | 3.64 | 1.71 |
| M3 | 1.45 | 17.03 | 16.24 | 7.33 | 3.64 | 1.71 |
| M4 | 5.78 | 68.14 | 64.94 | 29.31 | 14.60 | 6.82 |
| M5 | 28.44 | 335.17 | 319.44 | 144.19 | 71.62 | 33.56 |
| M6 | 4.50 | 53.00 | 50.51 | 22.80 | 11.32 | 5.31 |
| M7 | 2.89 | 34.07 | 32.47 | 14.66 | 7.28 | 3.41 |
| M8 | 31.36 | 369.59 | 352.24 | 158.99 | 78.97 | 37.01 |
| M9 | 44.96 | 529.95 | 505.08 | 227.98 | 113.23 | 53.07 |

Active substance:
cinnamic acid (5),
chrysin (6),
pinocembrin (7),
galangin (8),
apigenin (9),
kaempferol (10)
Model microorganism:
S. aureus ATCC 29293 (M1),
MRSA (M2),
MSSA (M3),
E. faecalis ATCC 9212 (M4),
E. faecalis VRE (M5),
E. coli ATCC 10536 (M6),
A. baumanii ATCC 43498 (M7),
P. aeruginosa ATCC 9027 (M8),
C. albicans ATCC 90028 (M9)

Overall antimicrobial effect (MIC) of each of the tested liquid propolis extracts is reached by a synergistic effect of several active substances 1-10. An interesting and completely unexpected thing is that the mixture of active substances 1-10 in small concentrations is more effective than that of much higher concentrations of certain (pure) active substances 1-10.

The formulation of the present invention is the most effective against Gram positive microorganisms such as Staphylococcus spp., but, as can be seen from Table 9, in a higher concentration it is also effective against some Gram-negative bacteria: E. coli and A. baumanii, as well as fungus C. albicans.

The Use of Standardized Liquid Propolis Extract According to the Present Invention The propolis extract as a pharmaceutical, cosmetic or agrochemical ingredient or food ingredient according to the present invention, contains standardized concentrations of highly bioactive substances:
(i) p-coumaric acid (1); 100-1,300 µg/mL;
(ii) trans-ferulic acid (2); 75-800 µg/mL;
(iii) caffeic acid (3); 25-300 µg/mL; and
(iv) 2-phenylethyl 3,4-dihydroxy-trans-cinnamate (4; CAPE); 40-400 µg/mL.

Due to the standardized content of key active substances 1-4, the liquid propolis extract according to the invention, represents an active pharmaceutical ingredient (API) for use in humans and animals, active cosmetic ingredient (ACI), or functional ingredient for food or animal feed, which is characterized by the following beneficial pharmacological effects:
(i) anti-inflammatory; see literature references 1, 8, 9, 11, 12, 13, 17;
(ii) antioxidative; see literature references 8, 9, 14, 15, 20;
(iii) immunomodulatory; see literature references 1, 8, 11, 13, 15, 17, 18, 19, 20;
(iv) hepatoprotective; see literature reference 9;
(v) antimicrobial; including also antibacterial, antiviral, antifungal and antiprotozoal; see literature references 9, 10, 12, 15, 16, 18;
(vi) antitumour; see literature references 9, 10, 11, 14, 19; and
(vii) anticancer; see literature references 11, 14.

Other valuable effects of the liquid propolis extract according to the invention, are fungicidal, bactericidal, virucidal, insecticidal and nematocidal effects in plant protection. Due to strong antioxidant activity, the liquid propolis extract according to the invention, indirectly strengthens plants and their resistance against abiotic stress factors and helps them against infections. Because of this, it is used as a plant strengthening agent; see literature references 21-25.

The liquid propolis extract according to the present invention is used as:
(i) an active pharmaceutical ingredient or excipient for the production of pharmaceutical products selected from the group consisting of: drugs, medicinal devices or remedies;
(ii) an active cosmetic ingredient or excipient for the production of cosmetic products;
(iii) a food ingredient for the production of functional food products, food supplements, or food for special nutritional purposes;
(iv) an active pharmaceutical ingredient or excipient for the production of veterinary products selected from the group consisting of: veterinary-medicinal products; animal feed; animal feed supplements; or remedies for veterinary use; or
(v) an active agrochemical ingredient or excipient for the production of agrochemical products selected from the group consisting of: fungicides, bactericides, virucides, insecticides, nematocides and plant strengtheners; what is especially suitable for ecological agriculture.

The Pharmaceutical Composition Based on the Said Standardized Liquid Propolis Extract According to the Present Invention Furthermore, the present invention discloses the pharmaceutical composition which is based on the said standardized liquid propolis extract as an active pharmaceutical ingredient (API). The pharmaceutical composition according to this invention consists of:
- (I) the liquid propolis extract according to the present invention; from 5-95% w/w; and,
- (II) one or more pharmaceutical excipients required for the final dosage form preparation selected from the group consisting of: a solution, suspension, gel, cream, ointment, spray for oral or nasal application; up to 100% w/w of the final composition;

where the said composition is characterized by quantitative contents of minimally two of four key active propolis substances, within the following values:
- (i) p-coumaric acid (1); from 10-1,300 µg/g;
- (ii) trans-ferulic acid (2); from 10-800 µg/g;
- (iii) caffeic acid (3); from 5-300 µg/g; and,
- (iv) 2-phenylethyl 3,4-dihydroxy-trans-cinnamate (4; CAPE); from 5-400 µg/g.

Thereby, the pharmaceutical excipients (auxiliary substances) are selected from the group consisting of: diluents, humectants, preservatives, chelating agents, antioxidants, thickeners, emollients, emulsifiers, tonicity agents and pH-control agents.

The diluent is a pharmaceutically acceptable liquid, selected from the group consisting of: purified water; ethanol; 1,2-propyleneglycol; liquid polyethylene glycols (PEG) such as PEG 200, PEG 400 or PEG 600; or mixtures of these substances.

The humectant is selected from the group consisting of: glycerol, sorbitol, 1,2-propylene glycol, or mixtures of these substances.

The preservative is selected from the group consisting of: parabens like methyl 4-hydroxybenzoate, ethyl 4-hydroxybenzoate, propyl 4-hydroxybenzoate, butyl 4-hydroxybenzoate; 4-chloro-m-cresol; triclosan; benzyl alcohol; 2-phenoxyethanol; benzoic acid and its salts like sodium benzoate; sorbic acid or its salts such as potassium sorbate; dehydroacetic acid (3-acetyl-2-hydroxy-6-methyl-4H-pyran-4-one); chlorhexidine and its salts like chlorhexidine digluconate; quaternary ammonium salts such as benzalkonium chloride or cetrimonium bromide; or mixtures of these substances.

The chelating agent is selected from the group consisting of: sodium or potassium salts of ethylenediamino tetraacetic acid (EDTA), diethylenetriamino pentaacetic acid (DTPA), nitrilotriacetic acid (NTA); soluble citrate salts like trisodium citrate dihydrate ($Na_3C_6H_5O_7 \cdot 2H_2O$); or mixtures of these substances. A typical chelating agent is disodium edetate dihydrate ($Na_2EDTA \cdot 2H_2O$).

The antioxidant is selected from the group consisting of: a-tocopherol and its esters such as a-tocopheryl succinate; ascorbic acid and its salts like sodium ascorbate; 2,6-di-tert-butyl-4-methylphenol (BHT); tert-butyl-anisole (BHA); or mixtures of these substances.

The thickener is selected from the group consisting of: cellulose gum like hydroxypropyl methylcellulose (HPMC), hydroxypropyl cellulose (HPC), hydroxyethyl cellulose (HEC), methyl cellulose (MC), sodium carboxymethyl cellulose (NaCMC); synthetic polymers such as polyvinyl alcohol (PVA), polyacrylic acid (PAA) and its copolymers, polyvinyl pyrrolidone (PVP); various gums like gum arabic, xanthan gum, tragacanth; alginic acid and its salts like sodium alginate; metal salts of higher fatty acids such as aluminium monostearate, aluminium distearate, aluminium tristearate; or mixtures of these substances.

The emollient is selected from the group consisting of: petroleum jelly; mineral oil; plant oils like almond, sunflower or olive oil; medium-chain triglycerides; natural or synthetic esters of higher fatty acids and monovalent alcohols such as isopropyl myristate or jojoba oil; waxes like beeswax; silicon oil; higher fatty acids like oleic or stearic acid; higher fatty alcohols such as cetyl alcohol; or mixtures of these substances.

The emulsifier is selected from the group consisting of: lanolin; ethoxylated lanolin; lanolin alcohols; ethoxylated lanolin alcohols; lecithin; hydrolized lecithin; mono- and diesters of glycerol and higher fatty acids such as glycerol monostearate; sorbitan esters of higher fatty acids like sorbitan monostearate; ethoxylated higher fatty alcohols such as polyoxyethylene(23) laurylether or polyoxyethylene (2) oleate wherein the number 23 or 2 represents the number of ethyleneoxide units; esters of ethoxylated sorbitan esters like polysorbate 60; water soluble soaps such as sodium stearate; water soluble sulphates of higher fatty alcohols like sodium lauryl sulphate; water soluble phosphates of fatty alcohols such as potassium cetyl phosphate; or mixtures of these substances.

The tonicity agent is employed mainly in pharmaceutical dosage forms that are applied on mucosa, e.g. nasal mucosa, and are selected from the group consisting of: sodium chloride (NaCl), glycerol, 1,2-propyleneglycol, or mixtures of these substances.

The pH-control agent includes pharmaceutically acceptable acids and bases for decreasing or increasing pH value and buffer systems. It is selected from the group consisting of: hydrochloric acid (HCl), sulphuric acid ($H_2SO_4$), phosphoric acid ($H_3PO_4$), citric acid, acetic acid, sodium hydroxide (NaOH), potassium hydroxide (KOH), ammonium hydroxide ($NH_4OH$), sodium dihydrogen phosphate ($NaH_2PO_4$), sodium hydrogen phosphate ($Na_2HPO_4$), sodium dihydrogen citrate ($NaH_2C_6H_5O_7$), sodium hydrogen citrate ($Na_2HC_6H_5O_7$), sodium citrate ($Na_3C_6H_5O_7$), or mixtures of these substances.

Preparation of the Pharmaceutical Composition According to the Present Invention The pharmaceutical composition from the present invention is prepared by the process which includes the following steps:
- (i) addition of standardized liquid propolis extract according to this invention into diluent and their homogenization;
- (ii) addition of one or more other excipients; and their homogenization;

where steps (i) and (ii) are carried out at temperature from 10-100° C., preferably at temperature from 20-60° C., during 1-5 minutes; followed by, in the case of the dosage form preparation of:
- (iii.a) solution or solution for spray; filtration of the final solution is performed, including sterile filtration if necessary;
- (iii.b) gel or suspension; addition of thickener and its homogenization is carried out;
- (iii.c) cream; preparation of fatty phase is conducted by mixing the emollient and emulsifier and their homogenization at temperature from 50-80° C., during 1-15 minutes, and then addition of the solution from the step (ii) heated to 50-80° C. is carried out, followed by emulsification with the use of high shear or high-pressure homogenizer, at temperature from 50-80° C., preferably from 55-65° C., during 1-30 minutes, with subsequent homogenization at temperature from 65-20° C., during 10-120 minutes; or at (iii.d) ointment; the mixing of the solution from the step (ii) with previously melted mixture of emollient and eventually emulsifier at temperature from 50-70° C., during 5-30 minutes, is performed, followed by homogenization at temperature from 70-20° C., during 10-120 minutes.

The procedures for preparation of the pharmaceutical composition from the present invention can include also various alternative common technological procedures for production of the said dosage forms, as is known to the person skilled in the art of pharmaceutical technology.

Representative examples of the pharmaceutical composition production according to the invention are described in Examples 11-16.

As a special example, here is the outlined final dosage form of a solution for intramammary application, which is disclosed in Example 11. In this case, the primary standardized liquid propolis extract, whose preparation is described in Example 9, is just diluted with the extraction solvent according to the invention; in this case with the mixture of polyethylene glycol 400 (97% w/w) and soybean lecithin (3% w/w), which is here in the function of the diluent. Thus obtained solution for intramammary application gives the quantitative content of key active substances 1-4 within the above-mentioned limits; see Table 16.

TABLE 16

Results of quantitative analysis of active substances 1-10 by high performance liquid chromatography (HPLC) of the pharmaceutical composition from the present invention; the dosage form of solution for intrammamary application; product from Example 11, characterized by the drug-to-extract (DER) weight ratio 1:2, diluted 10× for the purpose of HPLC analysis.[a]

| No. | Propolis active substance 1-10 | Concentration [µg/g] |
|---|---|---|
| 1 | para-coumaric acid (1) | 40.97 |
| 2 | trans-ferulic acid (2) | 52.18 |
| 3 | caffeic acid (3) | 17.73 |
| 4 | CAPE (4) | 52.25 |
| 5 | cinnamic acid (5) | 6.99 |
| 6 | chrysin (6) | 84.70 |
| 7 | pinocembrin (7) | 77.36 |
| 8 | galangin (8) | 43.37 |
| 9 | apigenin (9) | 15.24 |
| 10 | kaempferol (10) | 4.76 |

[a]HPLC analytical method is described in Example 3.

Figure 5:
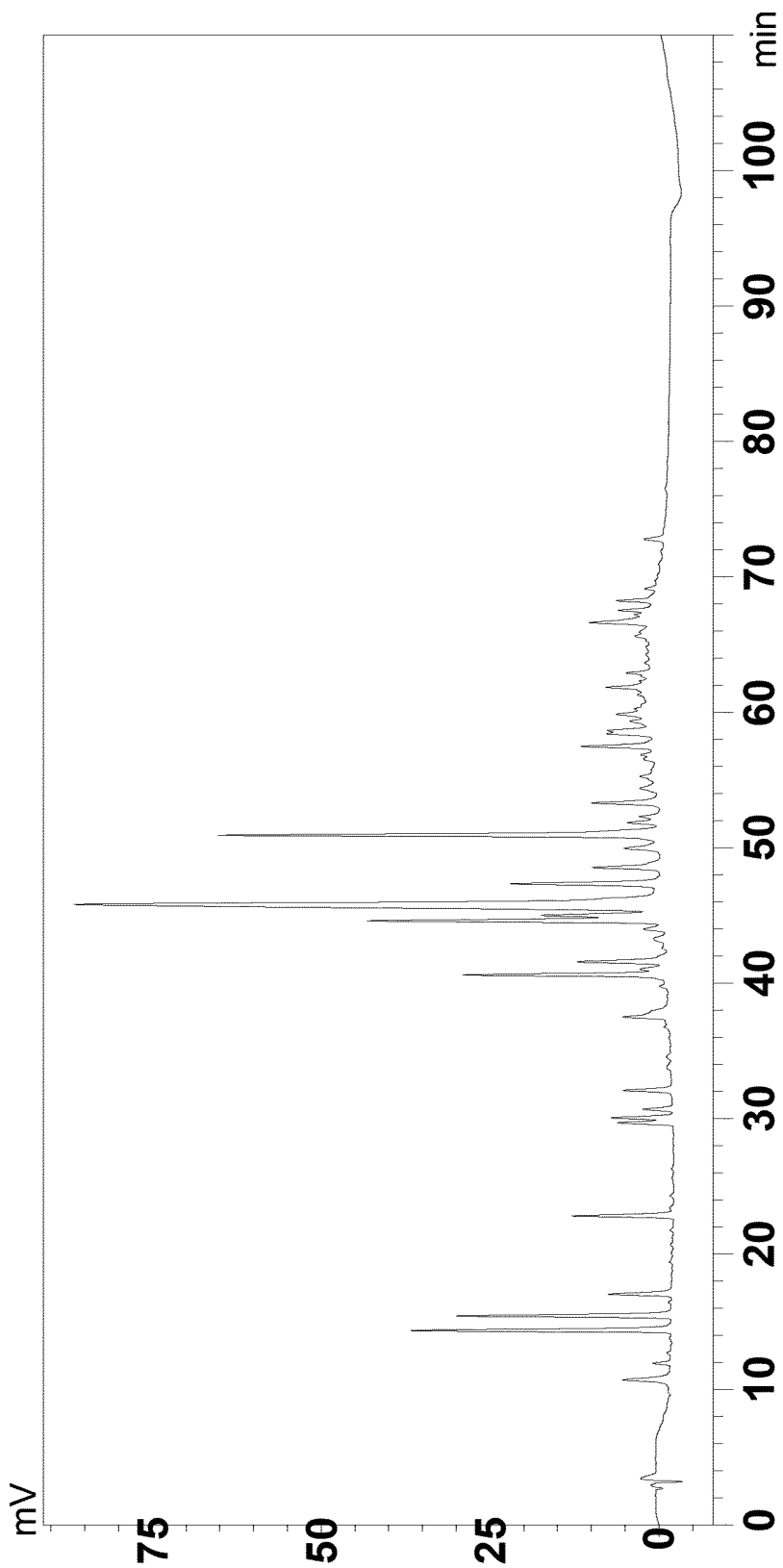
FIG. 5 shows a typical HPLC chromatogram of a quantitative analysis of the pharmaceutical formulation from this invention, product from Example 11.

Typical HPLC chromatogram from quantitative analysis of the present composition is shown in FIG. 5.

Studies of Pharmacological Effects of the Pharmaceutical Composition from the Present Invention Selected pharmacological effects of the composition from the present invention, in the dosage from the solution, product from Example 11, were studied in clinical studies in the therapy of:
(i) mastitis, udder inflammation in cows;
(ii) mastitis in goats; and,
(iii) wound healing in horses.

The Study of Mastitis Therapy in Cows

The study of mastitis treatment in cows was performed at five farms with dairy cattle of Holstein breed. Total of 86 cows were involved in the study or 339 quarters, where the udder quarter was used as a statistical unit. Animals were kept freely in deep bedding and fed with standard premix for dairy cattle without antibiotic addition. The study was approved by the Ethics committee for veterinary medicine. Healthy animals and quarters, without clinical symptoms of mastitis with somatic cell count (SCC) below 200,000/mL were included, as well as infected quarters with SCC higher than 200,000/mL. A randomized crossover clinical study of safety and efficacy was performed with intramammary (i.mam.) application of the composition from this invention, in the form of a solution, under terrain conditions. The composition from the present invention from Example 11 was applied three-times in all four quarters of the cow udder: during morning milking, evening milking and the next day after the morning milking. The detailed procedure is described in Example 17, while Table 17 represents the bacteriological cure for each pathogen identified in a certain number of quarters before the first i.mam. application.

TABLE 17

Effectiveness of bacteriological treatment/cure of mastitis in cows after i.mam. application of the formulation from the present invention from Example 11.[a]

| | | Formulation from Example 11 | | |
|---|---|---|---|---|
| No. | Pathogen | Number of treated quarters (N) | Number of bacterially cured quarters | % cured |
| 1 | Streptococcus uberis | 9 | 9 | 100 |
| 2 | Streptococcus spp. | 2 | 2 | 100 |
| 3 | CNS | 1 | 1 | 100 |
| 4 | Enterococcus sp. | 2 | 2 | 100 |
| 5 | E. coli | 3 | 3 | 100 |
| 6 | Corynebacterium spp. | 4 | 4 | 100 |
| 7 | Pasteurella spp. | 2 | 2 | 100 |
| 8 | Citrobacter spp. | 1 | 1 | 100 |
| 9 | Serratia | 1 | 1 | 100 |
| 10 | Bacillus | 1 | 1 | 100 |
| | Total: | 26 | 26 | 100 |

[a]The procedure for performing study is described in Example 17.

The three-times (two days) administration regimen of the composition from Example 11 provided a bacteriological cure in 100% cases within only 7 days.

In comparison, the cephalosporin-type antibiotic ceftiofur, achieves 66% bacteriological cure, but only after daily i.mam. application during 8 days, while after 5 days it yields the cure in only 54% cases; see literature reference 30. At subclinical mastitis caused by S. uberis, a two-day therapy with pirlimycin led to healing in 58.1% cases, while the therapies for 5 and 8 days provided the cure in 68.8% and 80% cases; see literature reference 30:

30) S. P. Oliver, B. E. Gillespie, S. J. Headrick, H. Moorehead, P. Lunn, H. H. Dowlen, D. J. Johnson, K. C. Lamar, S. T. Chester, W. M. Moseley: Efficacy of extended Ceftiofur intramammary therapy for treatment of subclinical mastitis in lactating dairy cows. J. Dairy Sci. 87 (2004) 2393-2400.

Alternatively, in mastitis therapy in cows, the composition from the present invention in the dosage form of suspension for intramammary application, as described in Example 12, can also be successfully used.

The Study in Mastitis Therapy in Goats

The study of mastitis treatment in goats was conducted on the farm of Alpine goats at the OPG Matijasec, Sigetec Ludbreski, Croatia, on 25 goats. All goats were diagnosed with subclinical mastitis in left and right udder halves. The goats whose milk tested positive to a microbiological survey, were divided into two groups: to one group, the composition from the present invention from Example 11 was applied, while to the other group, the intramammary suspension of amoxicillin and clavulanic acid (Klavuxil®; Genera, Croatia) was applied; all by three-times application regimen. The tolerability and bacteriological cure of the halves were monitored in parallel after i.mam. application of the composition from Example 11. Three-times (two days) application of the formulation from the present invention provided a bacteriological cure in 75% infected halves, and 85% after 14 days. This proved to be more effective than intramammary antibiotic administration that enabled bacteriological cure in 73.3% cases. The results of the study showed that mastitis treatment with the composition from Example 11, in goats can provide a bacteriological cure on time, without the use of antibiotics.

The detailed procedure of the study is described in Example 18, while the results of the bacteriological cure are presented in Table 18.

TABLE 18

Effectiveness of bacteriological treatment/cure of mastitis in goats after i.mam. application of the formulation from the present invention from Example 11 in comparison with antibiotic (a fixed combination of amoxicillin and clavulanic acid).[a]

| No. | Pathogen | Number of treated udder halves (N) | Number of bact. cured udder halves after 7 days | Number of bact. cured udder halves after 14 days | % cured |
|---|---|---|---|---|---|
| Antibiotic (amoxicillin + clavulanic acid) | | | | | |
| 1 | Staphylococcus spp. | 8 | 2 | 4 | 50 |
| 2 | S. aureus | 1 | 1 | 1 | 100 |
| 3 | Streptococcus spp. | 3 | 3 | 3 | 100 |
| 4 | S. uberis | 2 | 2 | 2 | 100 |
| 5 | Arcanobacterium pyogenes | 2 | 2 | 2 | 100 |
| | Total: | 15 | 9 | 11 | 73.3 |
| Formulation from Example 11 | | | | | |
| 1 | Staphylococcus spp. | 8 | 6 | 7 | 87.5 |
| 2 | S. aureus | 7 | 4 | 6 | 85.7 |
| 3 | Streptococcus spp. | 2 | 2 | 2 | 100 |
| 4 | S. uberis | 2 | 2 | 2 | 100 |
| 5 | Arcanobacterium pyogenes | 1 | 1 | 1 | 100 |
| | Total: | 20 | 15 | 17 | 85 |

[a]The procedure for performing study is described in Example 18.

Comparing the activity of i.mam. application of amoxicillin, as a wide spectrum antibiotic, which is suitable for the treatment of mastitis caused by pathogens found in the milk samples and the composition from Example 11, a stronger activity of the latter was proven. Seven days after the application of amoxicillin only 60% halves were cured, while the result for the composition from Example 11 was 75%. 14 days after the first application, the total percentage of bacteriologically cured halves at the antibiotic application was 73.3%, while for the tested composition was 85%.

From the said results, one can see a high efficacy in anti-inflammatory and antimicrobial activity of the composition from this invention, in the treatment of mastitis. The efficacy is higher than that of the classic therapy like the one with a fixed combination of amoxicillin and clavulanic acid as a wide spectrum antibiotic.

Alternatively, in mastitis therapy in goats, the composition from the present invention in the dosage form of suspension for intramammary application, as described in Example 12, can also be successfully used.

It can be concluded that the composition from this invention, beside its other properties, is characterized by antimicrobial activity against a series of bacteria and fungi, where the antimicrobial efficacy is, in comparison to classical antibiotics, higher in vivo than under in vitro conditions. It is not only an antimicrobial agent, but also an anti-inflammatory and immunomodulatory agent.

Immunomodulatory propolis effects are closely connected with its antioxidant effects and oxidative stress is an integral part of mastitis pathogenesis; see for example literature reference 31:

31) O. Atakisi, H. Oral, E. Atakisi, O. Merhan, S. Metin Pancarci, A. Ozcan, S. Marasli, B. Polat, A. Colak, S. Kaya: Subclinical mastitis causes alterations in nitric oxide, total oxidant and antioxidant capacity in cow milk, Res. Vet. Sci. 89 (2010) 10-13.

A Review of the Wound Healing Case in Horses

The case of wound healing on the front leg of a mare is described. It was a deep wound in the ergot area of the front leg, which arose when the hind leg gripped the front leg during landing. Before starting the administration of the composition from Example 11, the wound had been treated conservatively, unsuccessfully, with different preparations.

Then, the wound was washed with a physiological solution, dried and treated with the composition from Example 11 once a day during 5 days. The improvement like epithelization could be seen after 48 h and the full healing of the wound occurred after 96 h. The mare intensively limped over several days, while after that, no signs of lameness were observed. The recovery was complete. A detailed description of this case is described in Example 19.

Despite the fact that for more precise conclusions, a detailed clinical study has to be performed, it is clear to those skilled in the art, that the present composition effectively acts as a wound healing agent. Since it is known from literature that anti-inflammatory, antioxidant and epithelizing activities are important for the wound healing process, the stimulation of collagen synthesis, as with the composition from the present invention, together with proven antimicrobial activity, is part of the spectrum of pharmacological effects; for comparison, see literature reference 32:

32) S. Marinotti, E. Ranzato: Propolis: a new frontier for wound healing, Burns Trauma (2015) 3:9, doi 10.1186/s41038-015-0010-z.

The Use of Pharmaceutical Composition According to the Present Invention

The pharmaceutical composition from this invention is used for the treatment of diseases and conditions in humans and animals, from the groups of: inflammatory diseases; bacterial infections; fungal infections; viral diseases; autoimmune diseases; functional gastrointestinal disorders; for mucosal regeneration, burn treatment and wound healing; as well as cancer diseases.

Inflammatory diseases and conditions included are: gingivitis, periodontitis, laryngitis, gastritis, colitis, haemorrhoidal disease, dermatitis, outer ear inflammation, sinusitis, rhinitis, vaginitis and mastitis.

The pharmaceutical composition from this invention is used for the treatment of bacterial infections caused by bacteria from the groups of:

(i) Gram-positive bacteria: *Staphylococcus* spp.: *Staphylococcus aureus*, MRSA (methicillin-resistant *Staphylococcus aureus*), MSSA (methicillin-sensitive *Staphylococcus aureus*), *Staphylococcus intermedius*, *Staphylococcus pseudintermedius*; coagulase-negative staphylococci: *Staphylococcus epidermidis*, *Staphylococcus saprophyticus*, *Staphylococcus hyicus*; *Streptococcus* spp.: *Streptococcus uberis*, *Streptococcus bovis*, *Streptococcus dysgalactiae*, *Streptococcus agalactiae*, *Streptococcus canis*, *Streptococcus pyogenes*, *Streptococcus pneumoniae*, *Streptococcus oralis*, *Streptococcus thermophilus*; *Peptostreptococcus* spp.; *Corynebacterium* spp.: *Corynebacterium bovis*; *Trueperella pyogenes*; *Nocardia* spp.; *Bacillus subtilis*; *Bacillus cereus*; enterococci: *Enterococcus faecium*, *Enterococcus faecalis*; vancomycin-resistant enterococci (VRE): *Enterococcus casseliflavus*; and, (ii) Gram-negative bacteria: *Escherichia coli*; *Acinetobacter baumanii*; *Pseudomonas aeruginosa*; *Haemophilus influenzae*; *Salmonella choleraesuis*; *Yersinia enterocolitica*; *Enterobacter* spp. (*Enterobacter cloacae*); *Klebsiella* spp.: *Klebsiella pneumoniae*, *Klebsiella oxytoca*; *Shigella flexneri*; *Burkholderia cepacia*; *Proteus mirabilis*; *Proteus vulgaris*; *Aggreqatibacter actinomycetemcomitans*; *Actinomyces israelii*; *Bacteroides fragilis*; *Helicobacter pylori*; *Campylobacter coli*; *Campylobacter jejuni*; *Porphyromonas gulae*; *Porphyromonas salivosa*; *Porphyromonas denticanis*; *Prevotella intermedia*; *Treponema* spp.; *Bacteroides splanchnicus*.

Furthermore, the present pharmaceutical composition is used for the treatment of fungal infections caused by fungi such as: *Candida* spp.: *Candida albicans*, *Candida dubliniensis*, *Candida glabrata*, *Candida kruzei*, *Candida tropicalis*, *Candida parapsilosis*; *Aspergillus* spp.: *Aspergillus niger*, *Aspergillus versicolor*; *Penicillium pinophilum*; *Paecilomyces variotii*; *Trichoderma virens*; *Chaetomium globosum*; and *Malassezia pachydermatis*.

Also, the composition from the invention is used for the treatment of viral diseases caused by viruses such as: Herpes simplex virus (HSV); Human papillomavirus (HPV); Epstein-Barr virus (EBV); Cytomegalovirus (CMV); poliovirus; influenza A and B viruses; retroviruses; vaccinia virus; common cold viruses: rhinovirus, picornavirus, human parainfluenza virus (HPIV), human metapneumovirus (HMPV), coronavirus, adenoviruses, human respiratory syncytial virus (HRSV), enteroviruses.

Alternatively, the pharmaceutical composition according to the present invention is used for the treatment of autoimmune diseases such as: psoriasis, systemic lupus erythematosus, rheumatoid arthritis, inflammatory bowel disease, coeliac disease and multiple sclerosis.

Additionally, the pharmaceutical composition from this invention is used for the treatment of cancer diseases such as: cancer of skin and mucosa, gastrointestinal tumors, colorectal carcinoma.

The pharmaceutical composition from the present invention is used for treatment of functional gastrointestinal disorders as follows: disorders of esophagus, stomach, duodenum, small intestine and colon, centrally mediated gastrointestinal pain, gallbladder and sphincter of Oddi disorders, anorectal disorders, children and adolescent-specific gastrointestinal disorders.

Specifically, the composition from the present invention is used for the treatment of mastitis in animals.

EXAMPLES

General Remarks

As the primary propolis, the crude propolis of poplar type, from *Hedera* Ltd was used. Ethanol (96%) and polyethylene glycol 200, 400 and 600, and powderous soybean lecithin (SL) were purchased from Fagron Croatia Ltd (HR). Rapeseed lecithin (RL) and hydrolysed rapeseed lecithin (HRL) were purchased from Pfannenschmidt (DE). Deoiled sunflower lecithin (SUL) was purchased from Barentz (NL). Aluminium distearate was purchased from Sigma-Aldrich (US). All other starting raw materials were purchased from local suppliers.

The samples of chemically pure compounds for the analytical purpose: p-coumaric acid (1; ≥98% HPLC), trans-ferulic acid (2; 99%), caffeic acid (3; ≥98% HPLC), 2-phenethyl 3,4-dihydroxy-trans-cinnamate (CAPE; 4; ≥97% HPLC), trans-cinnamic acid (5; ≥96.5% GC), chrysin (6; ≥98% HPLC), pinocembrin (7; ≥95% TLC), galangin (8; ≥95% HPLC), apigenin (9; ≥99% HPLC) and kaempferol (10; ≥90% HPLC), which served as quantitative analytical standards for the determination of their quantitative content in the liquid propolis extracts, were purchased from the company Sigma-Aldrich (US).

The term room temperature refers to the temperature interval from 20-° C. Abbreviation "min" stands for minute. The yield (% from theoretical yield) is expressed as weight (% w/w) percent of isolated liquid propolis extract against the mass of starting extraction solvent (ethanol, PEG, ethanol+lecithin, PEG+lecithin). The quantitative content of active substances 1-10 in the liquid propolis extracts are expressed as mass concentration ($\gamma$) in micrograms per millilitre [µg/mL], while its quantitative composition in the pharmaceutical composition from this invention, is expressed in micrograms per gram of the final product (dosage form) [µg/g].

Example 1. Preparation of Liquid Propolis Extract by the Use of 96% Ethanol as the Extraction Solvent Propolis pre-treatment before the extraction: Sample of the crude propolis (poplar-type; 1 kg) was chilled in a refrigerator at −20° C. for minimally 1 h. Then the sample was milled in the mill.

Extraction with 96% ethanol: Ethanol (96%; 70.00 g) was added to milled propolis (30.00 g). Thus obtained mixture was allowed to stand at room temperature during 72 h with periodical stirring. Then, the mixture was filtered through filter paper (black ribbon), yielding 60.00 g (85.7%) liquid propolis extract in the form of deep brown-coloured solution with slightly intensive propolis odour.

For the purpose of testing the minimal inhibitory concentration (MIC) of alcohol propolis extract described in Example 10, the same procedure was repeated at the drug-to-extract (DER) ratio 1:2.

Example 2. Preparation of Liquid Propolis Extract by the Use of Polyethylene Glycol 400 as the Extraction Solvent Milled propolis whose pre-treatment is described in Example 1 (30.00 g) was mixed with polyethylene glycol 400 (PEG 400; 70.00 g). Thus obtained mixture was allowed to stand at room temperature during 72 h with periodical stirring. Then, the mixture was filtered through the filter paper (black ribbon). This yielded in 55.00 g (78.6%) a liquid propolis extract in the form of a deep brown viscous liquid, of slightly intensive odour resembling propolis.

For the purpose of testing the minimal inhibitory concentration (MIC) of polyethylene glycol propolis extract described in Example 10, the same procedure was repeated at the drug-to-extract (DER) ratio 1:2.

Example 3. HPLC Analytical Method for Quantitative Determination of Active Substances 1-10 in Liquid Propolis Extracts Quantitative analyses by high performance liquid chromatography (HPLC) were performed with the method developed specially for the purpose of monitoring the key active substances 1-4, and accompanied active ingredients 5-10 from propolis.

The samples of commercially available standards of active substances 1-10 are prepared for analysis by dilution with ethanol: water mixture, 75:25, V/V, up to the concentration of 100 μg/mL.

The samples of liquid propolis extracts (100 μL) according to the present invention were, before the analysis, diluted with ethanol: water mixture, 75:25, V/V (900 μL), in ratio 1:10 w/w (10× dilution).

Analyses were carried out on the Shimadzu LC201CHT instrument, equipped with an autosampler, pump, degasser, column oven, and UV-VIS detector, under the following conditions:
 (i) chromatographic column: Ascentis express; C18; dimensions: 15 cm×3.0 mm; diameter of particles in the column: 2.7 μm;
 (ii) mobile phase: A=0.1% formic acid aqueous solution, B=methanol; gradient: 0 min, 80% A, 20% B; 3 min, 70% A, 30% B; 60 min, 20% A, 80% B; 90 min, 20% A, 80% B; 100 min, 70% A, 30% B; 105 min, 80% A, 20% B;
 (iii) column temperature: 30° C.;
 (iv) flow: 0.25 mL/min;
 (v) analysis time: 110 min;
 (vi) wavelength on UV-VIS detector: for detection: 370 nm, for integration: 290 nm;
 (vii) injection volume: 10 μL;
 (viii) pressure: 210-290 bars.

Under the said conditions, the key active substances 1~4 and accompanied ingredients 5-10 have the following retention times ($t_R$):
 (i) $t_R$ [p-coumaric acid (1)]=14.13 min; $t_R$ [trans-ferulic acid (2)]=15.31 min; $t_R$ [caffeic acid (3)]=10.57 min; $t_R$ [2-phenethyl 3,4-dihydroxy-trans-cinnamate; CAPE (4)]=48.62 min;
 (ii) $t_R$ [trans-cinnamic acid (5)]=29.76 min; $t_R$ [chrysin (6)]=44.68 min; $t_R$ [pinocembrin (7)]=47.39 min; $t_R$ [galangin (8)]=49.94 min; $t_R$ [apigenin (9)]=37.72 min; $t_R$ [kaempferol (10)]=36.87 min.

The retention times of the key propolis active substances 1-4 and accompanied active ingredients 5-10 are given in Table 1.

Example 4. Preparation of Standardized Liquid Propolis Extracts by the Use of the Extraction Solvent Based on Mixture of Ethanol and Lecithin The milled propolis, whose pre-treatment is described in Example 1, (30.00 g) was mixed with the extraction solvent of the following composition (experiments E1-8):

E1: 96% ethanol (67.00 g; 95.7%) and soybean lecithin (SL; 3.00 g; 4.3%);
E2: 96% ethanol (60.00 g; 85.7%) and soybean lecithin (SL; 10.00 g; 14.3%);
E3: 96% ethanol (50.00 g; 71.4%) and soybean lecithin (SL; 20.00 g; 28.6%);
E4: 96% ethanol (40.00 g; 57.1%) and soybean lecithin (SL; 30.00 g; 42.9%);
E5: 96% ethanol (67.00 g; 98.9%) and rapeseed lecithin (RL; 3.00 g 25%-preparation; 0.75 g lecithin; 1.1%); theoretical yield in E5=67 g ethanol+0.75 g lecithin=67.75 g;
E6: 96% ethanol (60.00 g; 96.0%) and rapeseed lecithin (RL; 10.00 g 25%-preparation; 2.50 g lecithin; 4.0%); theoretical yield in E6=60 g ethanol+2.50 g lecithin=62.50 g;
E7: 96% ethanol (67.00 g; 97.8%) and hydrolysed rapeseed lecithin (HRL; 3.00 g 50%-preparation; 1.50 g hydrolysed rapeseed lecitin; 2.2%); theoretical yield in E7=67 g ethanol+1.50 g lecithin=68.50 g;
E8: 96% ethanol (60.00 g; 92.3%) and hydrolysed rapeseed lecithin (HRL; 10.00 g 50%-preparation; 5.00 g lecithin; 7.7%); theoretical yield in E8=60 g ethanol+5.00 g lecithin=65.00 g.

Thus obtained mixture was stirred at room temperature for 1 h and allowed to stand at room temperature for 72 h with periodical stirring. Then, the mixture was filtered through the filter paper (black ribbon). This yielded in 50-60 g (71.0-85.7%) a liquid propolis extract in the form of a deep brown viscous liquid, of slightly intensive odour resembling propolis.

Thus prepared primary liquid propolis extract underwent quantitative analyses of the content of the key active substances 1-4 and also accompanying ingredients 5-10, according to the analytical method described in Example 3. The results are presented in Tables 3 and 4.

Such prepared primary liquid propolis extracts in extraction solvents (ES) described in experiments E1-E8 with known quantitative contents of active substances 1-4, were standardized by dilution with the same ES which was employed in the extraction step, up to the desired level of the quantitative composition of active substances 1-4 according to the present invention.

Example 5. Preparation of Standardized Liquid Propolis Extracts by the Use of the Extraction Solvent Based on Mixture of Polyethylene Glycol 400 and Lecithin The milled propolis, whose pre-treatment is described in Example 1, (30.00 g) was mixed with the extraction solvent of the following composition (experiments E1-E8):

E1: polyethyleneglycol 400 (PEG 400; 67.00 g; 97%) and soybean lecithin (SL; 3.00 g; 3%);
E2: polyethylene glycol 400 (PEG 400; 60.00 g; 90%) and soybean lecithin (SL; 10.00 g; 10%);
E3: polyethylene glycol 400 (PEG 400; 67.00 g; 98.9%) and rapeseed lecithin (RL; 3.00 g 25%-preparation; 0.75 g lecithin; 1.1%); theoretical yield in E3=67 g PEG 400+0.75 g lecithin=67.75 g;
E4: polyethylene glycol 400 (PEG 400; 60.00 g; 96.0%) and rapeseed lecithin (RL; 10.00 g 25%-preparation; 2.50 g lecithin; 4.0%); theoretical yield in E4=60 g PEG 400+2.50 g lecithin=62.50 g;
E5: polyethylene glycol 400 (PEG 400; 67.00 g; 97.8%) and hydrolysed rapeseed lecithin (HRL; 3.00 g 50%- preparation; 1.50 g hydrolysed lecithin; 2.2%); theoretical yield in E5=67 g PEG 400+1.50 g lecithin=68.50 g;

E6: polyethylene glycol 400 (PEG 400; 60.00 g; 92.3%) and hydrolysed rapeseed lecithin (HRL; 10.00 g 50%-preparation; 5.00 g lecithin; 7.7%); theoretical yield in E6=60 g PEG 400+5.00 g lecithin=65.00 g.

Thus obtained mixture was stirred at room temperature for 1 h and allowed to stand at room temperature for 72 h with periodical stirring. Then, the mixture was filtered through the filter paper (black ribbon). This yielded in 45-55 g (69.0-78.6%) a liquid propolis extract in the form of a deep brown viscous liquid, of slightly intensive odour resembling propolis.

Thus prepared primary liquid propolis extract underwent quantitative analyses of the content of the key active substances 1-4 and also accompanying ingredients 5-10, according to the analytical method described in Example 3. The results are presented in Tables 5 and 6.

Such prepared primary liquid propolis extracts in extraction solvents (ES) described in experiments E1-E6, with known quantitative contents of active substances 1-4, were standardized by dilution with the same ES which was employed in the extraction step, up to the desired level of the quantitative composition of active substances 1-4 according to the present invention.

Example 6. Preparation of Standardized Liquid Propolis Extracts by the Use of the Extraction Solvent Based on Mixture of Polyethylene Glycol 200 and Soybean Lecithin The milled propolis, whose pre-treatment is described in Example 1, (30.00 g) was mixed with the extraction solvent, the mixture of polyethylene glycol 200 (149.85 g; 99.9%) and soybean lecithin (SL; 0.15 g; 0.1%). Thus obtained mixture was stirred at room temperature for 1 h and allowed to stand at room temperature for 48 h with periodical stirring. Then, the mixture was filtered through the filter paper (black ribbon). This yielded in 137.00 g (91.3%) a liquid propolis extract in the form of a deep brown viscous liquid, of slightly intensive odour resembling propolis.

Then, a quantitative HPLC analysis according to the method described in Example 3 was performed to get the quantitative content of the key active substances 1-4. The filtrate was diluted with the same extraction solvent, mixture of polyethylene glycol 200 and soybean lecithin (SL), 99.9:0.1 w/w, up to the total level of the active substances 1-4 content, according to the specification of the standardized liquid extract from the present invention.

Example 7. Preparation of Standardized Liquid Propolis Extracts by the Use of the Extraction Solvent Based on Mixture of Polyethylene Glycol 600 and Deoiled Sunflower Lecithin The milled propolis, whose pre-treatment is described in Example 1, (30.00 g) was mixed with the extraction solvent, the mixture of polyethylene glycol 600 (PEG 600; 297,00 g; 99%) and deoiled sunflower lecithin (SUL; 3.00 g; 1.0%). Thus obtained mixture was heated to 70° C. and intensively stirred for 3 h. Then the mixture was cooled to room temperature and filtered through the filter paper (black ribbon). This yielded in 261.00 g (87.0%) a liquid propolis extract in the form of a deep brown viscous liquid, of slightly intensive odour resembling propolis.

Then, a quantitative HPLC analysis according to the method described in Example 3 was performed, from which the quantitative content of the key active substances 1-4 was determined. The filtrate was diluted with the same extraction solvent, mixture of polyethylene glycol 600 and deoiled sunflower lecithin (SUL), 99:1 w/w, up to the total level of the active substances 1-4 content, according to the specification of the standardized liquid extract from this invention.

Example 8. Preparation of Standardized Liquid Propolis Extracts by the Use of the Extraction Solvent Based on Mixture of Polyethylene Glycol 200, Polyethylene Glycol 600 and Hydrolysed Rapeseed Lecithin The milled propolis, whose pre-treatment is described in Example 1, (30.00 g) was mixed with the extraction solvent, the mixture of polyethylene glycol 200 (PEG 200; 150.00 g; 50%), polyethylene glycol 600 (139.50 g; 46.5%), and hydrolysed rapeseed lecithin (HRL; 10.50 g; 3.5%). Thus obtained mixture was heated at 100° C. with intensive stirring for 3 h. Then the mixture was cooled to room temperature and filtered through the filter paper (black ribbon). This yielded in 245.00 g (81.7%) a liquid propolis extract in the form of a deep brown viscous liquid, of slightly intensive odour resembling propolis. Then, quantitative HPLC analysis according to the method described in Example 3 was performed, from which the quantitative content of the key active substances 1-4 was determined. The filtrate was diluted with the same extraction solvent, mixture of polyethylene glycol 200, polyethylene glycol 600, and hydrolysed rapeseed lecithin (HRL), 50:46.5:3.5, w/w/w, up to the total level of the active substances 1-4 content, according to the specification of the standardized liquid extract from this invention.

Example 9. Preparation of Standardized Liquid Propolis Extracts by the Use of Polyethylene Glycol 400 and Soybean Lecithin Mixture The milled propolis, whose pre-treatment is described in Example 1, (30.00 g) was mixed with the extraction solvent, the mixture of polyethylene glycol 400 (PEG 400; 87.30 g; 97% m/m) and soybean lecithin (SL; 2.70 g; 3% w/w). Thus obtained mixture was allowed to stand to macerate with periodical stirring for 72 h. Then, the mixture was filtered through the filter paper (800 pores/cm$^2$). This gave 50-55 g of a deep brown viscous liquid, of intensive odour resembling propolis. Thus obtained product was diluted with the same extraction solvent up to the mass of 60.00 g. In this manner, the resulting extract of drug-to-extract (DER) ratio 1:2 was obtained, or, said 60 g of extract from 30 g of starting propolis.

Such prepared liquid propolis extract was, for the purpose of the pharmaceutical composition preparation, from this invention:

(I) subjected to quantitative HPLC analysis according to the method described in Example 3 for determination of active substances 1-4, and subsequently, with regard to real mass concentration of active substances 1-4 in such a prepared extract, (II) standardized by dilution with pure (fresh) solvent mixture: polyethylene glycol 400 (97% w/w) and soybean lecithin (3% w/w);

up to the mass concentration of active substances 1-4:
  (i) p-coumaric acid (1); 10-1,300 µg/mL;
  (ii) trans-ferulic acid (2); 10-800 µg/mL;
  (iii) caffeic acid (3); 5-300 µg/mL; and,
  (iv) 2-phenethyl 3,4-dihydroxy-trans-cinnamate (4; CAPE); 5-400 µg/mL;
divided with the factor X/100, wherein X=weight percentage %, w/w, of said standardized liquid propolis extract within the formulation of the pharmaceutical composition.

Example 10. Determination of Antimicrobial Efficacy of Standardized Liquid Extracts According to the Present Invention. Determination of Minimal Inhibitory Concentration (MIC) on Model Pathogenic Microorganisms The minimal inhibitory concentrations (MIC) of standardized liquid propolis extracts according to this invention were determined, with the use of the product from Example 9, in comparison with analogous liquid propolis extracts obtained with 96% ethanol (product from Example 1) or PEG 400 (product from Example 2), according to the directions of CLSI and EUCAST methods; see literature references 26-29.

Antimicrobial efficacy was tested under in vitro conditions on ATCC strains of the following model pathogenic microorganisms (M): *Staphylococcus aureus* ATCC 29293 (M1); methicillin-resistant *Staphylococcus aureus*; MRSA (MFBF collection; M2); methicillin-sensitive *Staphylococcus aureus*; MSSA (MFBF collection; M3); *Enterococcus faecalis* ATCC 9212 (M4); *Enterococcus faecalis* VRE (MFBF collection) (M5); *Escherichia coli* ATCC 10536 (M6); *Acinetobacter baumanii* ATCC 43498 (M7); *Pseudomonas aeruginosa* ATCC 9027 (M8); and *Candida albicans* ATCC 90028 (M9).

The serial microdilution procedure was conducted in order to determine the minimal inhibitory concentrations (MIC) of the extracts. Cell suspensions were prepared from the parent culture in PBS buffer (pH 7.4), and these were adjusted to 0.5 McFarland units by nephelometry. The testing was performed in serial dilution in 96-well microtiter plates in range from 100 to 0.7125 µg/mL, by addition of 100 µL of the solution of propolis extract dissolved in Mueller Hinton broth. After inoculation 100 µL of each bacterial culture adjusted to $10^5$ cfu/mL, plates were incubated for 24 h at 37° C. MIC was determined by addition of 10 µL of 0.5 mg/mL solution of 2,3,5-triphenyl-2H-tetrazolium chloride (TTC; redox indicator) per single well, and after the incubation for 4 h at 30° C., the absorbance was determined by spectrophotometry at wavelength 490 nm.

The MIC values were determined as the propolis extract concentration at which 80% reduction in bacteria occurred ($MIC_{80}$).

For fungal species, the MIC values were determined in RPMI medium with additional glucose, by the same scheme as with bacteria. After incubation (48 h, 37° C., aerobic conditions, in dark), XTT (redox indicator) was added in combination with menadion, and the absorbance was determined by spectrophotometry at wavelength 540 nm.

The MIC values were determined as the propolis extract concentration at which 80% reduction in bacteria or fungi occurred ($MIC_{80}$).

The negative control contained only the medium and the solvent (without added microorganisms and propolis), while the positive control was exposed to the influence of antibiotic or antifungal agents.

By in vitro determination of antimicrobial activity of the propolis solution, the minimal inhibitory concentrations ($MIC_{80}$) were measured, and shown in Table 9 in the form of dilution (%) of the liquid extract in a given solvent. The starting liquid propolis extract was obtained at the drug-to-extract (DER) weight ratio 1:2; product from Example 9. If the dilution of the liquid extract is larger, meaning that the concentration of active substances 1-10 is lower for MIC, the resulted antimicrobial effect of the tested extract is higher.

The results are presented in Table 9.

In Tables 10-15 the calculated values for mass concentration (γ) in [µg/mL] for each particular active substance 1-10 are given (from each of three examined liquid propolis extracts) on which each particular extract achieved the MIC. Extracts were obtained with the following extraction solvents (ES): 96% ethanol (product from Example 1), polyethylene glycol 400 (PEG 400; product from Example 2), and mixture of PEG 400 (97% w/w) and soybean lecithin (3% w/w) (product from Example 9). These were determined from primary liquid extracts where the DER is 1:2; divided by the dilution (factor) at which the corresponding MIC was achieved.

Example 11. Preparation of the Composition from the Present Invention in the Dosage Form of Solution for Intramammary Application with Minimally 150 µg/g Active Substances 1-4

Formulation (for 100 g Solution):
  (1) 50.00 g (50.00% w/w) liquid propolis extract according to this invention, product from Example 9, standardized on minimally 300 µg/mL active substances 1-4
  (2) 50.00 g (20.00% w/w) polyethylene glycol 400

Preparation: Ingredients (1) and (2) were mixed and homogenized by stirring at room temperature for 5 minutes. The solution was filtered through filter paper and filled into intramammary injectors per 4-8 g.

Solution composition: minimally 150 µg/g total concentration of active substances 1-4. The results of quantitative HPLC analysis are presented in Table 16, while the corresponding typical HPLC chromatogram is given in FIG. 5.

Example 12. Preparation of the Composition from the Present Invention in the Dosage Form of Suspension for Intramammary Application with Minimally 100 µg/g Active Substances 1-4

Formulation (for 100 g Suspension):
  (1) 77.00 g (77.00% w/w) liquid propolis extract according to this invention, product from Example 9, standardized on minimally 150 µg/mL active substances 1-4
  (2) 20.00 g (20.00% w/w) polyethylene glycol 4000
  (3) 3.00 g (3.00% w/w) aluminium distearate Preparation: Polyethylene glycol was melted (2) at 60° C., and aluminium distearate (3) was added and homogenized at this temperature for 15 minutes. Then, the mixture was cooled with stirring and the propolis extract (1) was added at 40-45° C. The mixture was further cooled to room temperature with stirring and additionally homogenized at room temperature for 15 minutes. A pale-yellow viscous suspension was obtained, which was further filled into intramammary injectors per 4-8 g.

Example 13. Preparation of the Composition from the Present Invention in the Dosage Form of Gel with Minimally 250 µg/g Active Substances 1-4

Formulation (for 100 g Gel):
- (1) 30.00 g (30.00% w/w) liquid propolis extract according to this invention, product from Example 9, standardized on minimally 850 µg/mL active substances 1-4
- (2) 2.00 g (2.00% w/w) Carbopol 940
- (3) 1.00 g (1.00% w/w) polysorbate 60
- (4) 0.20 g (0.20% w/w) potassium sorbate
- (5) 0.30 g (0.30% w/w) sodium benzoate
- (6) 0.30 g (0.30% w/w) citric acid, anhydrous
- (7) q.s. sodium hydroxide (20% solution)
- (8) ad 100% purified water Preparation: To 30 g of liquid propolis extract according to the present invention, (2) was added and homogenized by stirring at room temperature during 20 minutes. Then, 50 g purified water (8) was added and homogenized by stirring at room temperature for 5 minutes. After that, ingredients (3-6) were added and dissolved by stirring for 10 minutes. Then, the pH value was adjusted to 5.5-6 with (7). To thus obtained gel, the remaining amount of purified water was added, up to 100 g total mass and homogenized by stirring at room temperature for 15 minutes, with final de-aeration of the product.

Gel composition: minimally 250 µg/g total concentration of active substances 1-4.

Example 14. Preparation of the Composition from the Present Invention in the Dosage Form of Cream with Minimally 100 µg/g Active Substances 1-4

Formulation (for 100 g Cream):
- (1) 20.00 g (20.00% w/w) liquid propolis extract according to this invention, product from Example 9, standardized on minimally 500 µg/mL active substances 1-4
- (2) 5.00 g (5.00% w/w) polysorbate 60
- (3) 5.00 g (5.00% w/w) lanolin, anhydrous
- (4) 2.00 g (2.00% w/w) beeswax, white
- (5) 8.00 g (8.00% w/w) cetyl alcohol
- (6) 8.00 g (8.00% w/w) petroleum jelly, white
- (7) 10.00 g (10.00% w/w) mineral oil, thick
- (8) 0.20 g (0.20% w/w) 4-chloro-m-cresol
- (9) ad 100% purified water Preparation: Oil phase was prepared by melting the mixture of ingredients (2-7) at 65-70° C. during 15-20 minutes until the formation of almost colourless oily liquid. The aqueous phase was prepared by dissolution of (8) and (1) in purified water, with subsequent heating to 65-70° C. with stirring. Then, the aqueous phase was slowly added into the oily phase with intensive mixing, preferably with homogenizer that enables high shear homogenization, from 1,000-3,000 revolutions-per-minute (r.p.m.), during 15-20 minutes. Thus obtained emulsion was further intensively stirred with gradual cooling at temperatures from 65-20° C. during 30 minutes.

Cream composition: minimally 100 µg/g total concentration of active substances 1-4.

Example 15. Preparation of the Composition from the Present Invention in the Dosage Form of Ointment with Minimally 500 µg/g Active Substances 1-4

Formulation (for 100 g Ointment):
- (1) 50.00 g (50.00% w/w) liquid propolis extract according to this invention, product from Example 9, standardized on minimally 1,000 µg/mL active substances 1-4
- (2) 10.00 g (10.00% w/w) polyethylene glycol 400
- (3) 40.00 g (40.00% w/w) polyethylene glycol 4000

Preparation: Ingredients (1-3) were carefully mixed and heated to 60° C., homogenized by stirring for 5 minutes and gradually cooled to room temperature with mixing.

Ointment composition: minimally 500 µg/g total concentration of active substances 1-4.

Example 16. Preparation of the Composition from the Present Invention in the Dosage Form of Nasal Spray with Minimally 50 µg/g Active Substances 1-4

Formulation (for 100 g Solution for Spray):
- (1) 5.00 g (5.00% w/w) liquid propolis extract according to this invention, product from Example 9, standardized on minimally 1,000 µg/mL active substances 1-4
- (2) 0.60 g (0.60% w/w) sodium chloride
- (3) 0.10 g (0.10% w/w) polysorbate 60
- (4) 0.10 g (0.10% w/w) potassium sorbate
- (5) 0.10 g (0.10% w/w) sodium benzoate
- (6) 0.20 g (0.20% w/w) citric acid, anhydrous
- (7) 0.01 g (0.01% w/w) sodium edetate ($Na_2EDTA \cdot 2H_2O$)
- (8) ad 100% purified water Preparation: To 90 g purified water (1), ingredients (2-7) were added and dissolved by stirring at room temperature during 15 minutes. Then, (1) was added and the mixture was homogenized at room temperature for 15 minutes. After that, the solution was filtered through a sterile 0.2 µm filter and filled into suitable sterile bottles equipped with closure and spray-pumps for nasal application.

Solution composition: minimally 50 µg/g total concentration of active substances 1-4.

Example 17. The Study of Anti-Inflammatory Activity of the Composition from the Present Invention in the Form of Intramammary Solution from Example 11 in Mastitis Treatment of Dairy Cows The study of mastitis treatment in cows was performed at five farms of dairy cattle of Holstein breed. Total of 86 cows were involved in the study or 339 quarters, where the udder quarter was used as a statistical unit. Animals were kept freely in deep bedding and fed with a standard premix for dairy cattle without antibiotic addition. The study was approved by the Ethics committee for veterinary medicine. Healthy animals and quarters, without clinical symptoms of mastitis with somatic cell count (SCC) below 200,000/mL were included, as well as infected quarters with SCC higher than 200,000/mL. A randomized crossover clinical study of safety and efficacy was performed with intramammary (i.mam.) application of the composition from this invention in the form of a solution, under terrain conditions. The composition from the present invention from Example 11, was applied three-times in all four quarters of the cow udder: during morning milking, evening milking and on next day after the morning milking. First the tolerability of the composition in intramammary application was tested. The changes in cows' behaviour were monitored, as well as the macroscopic appearance of the udder (edema and redness), milk and udder sensitivity to touch. The change of somatic cell count (SCC) in milk was monitored from the period before the first i.mam. application of the composition, to 7. day from the first application. The milk samples, and also the quarters, were grouped depending on whether the SCC was elevated or below 200,000/mL, and whether the samples were positive or negative against a bacteriological survey; see literature reference 33:

33) European Medicines Agency (1992): Local Tolerance of Intramammary Preparations in Cows. Directive 81/852/EEC.

Then, the efficacy testings of the bacteriological cure were carried out with the propolis composition according to the directions of European Medicinal Agency (EMA), what is the only efficacy measure for i.mam. formulations in the treatment of subclinical mastitis. It is defined as an absence of previously confirmed pathogen in a sample of milk collected within certain periods of time after the i.mam. application of a given formulation; see literature reference 34:

34) European Medicines Agency (2017): Guideline on the conduct of efficacy studies for intramammary products for use in cattle. CVMP. EMA/CVMP/344/1999-Rev.2.

The milk sampling was performed by standard methodology. The microbiological survey was carried out according to the standard directions; see literature reference 35:

35) J. W. Hogan: Laboratory handbook on bovine mastitis. National Mastitis Council (1999) Madison, Wisconsin, SAD.

The results of bacteriological healing from mastitis in cows are presented in Table 17.

Example 18. The Study of Anti-Inflammatory Activity of the Composition from the Present Invention in the Form of Intramammary Solution from Example 11 in the Mastitis Treatment of Goats The study of mastitis treatment in goats was conducted on 25 goats with diagnosed subclinical mastitis in the left and right udder halves. The goats whose milk was positive to a microbiological survey were divided into two groups: to one group, the composition from the present invention from Example 11 was applied, while to the other group, the intramammary suspension of amoxicillin and clavulanic acid (Klavuxil®; Genera, Croatia) was applied; all by three-times application regimen.

The tolerability and bacteriological cure of the halves were monitored in parallel after i.mam. application of the composition from Example 11. The preparations were applied by the three-times (two days) regimen with the said antibiotic or the composition from the Example 11.

During the study, the goats were kept in a stable in deep bedding. There were 170 goats in lactation with average production of 500-600 kg of milk per goat during one lactation that lasts about 300 days. They were fed with hay as desired, minimally with 2 kg per goat, and with the premix containing 16% proteins, about 1 kg per goat; divided in two portions during morning and evening milking. 2% vitamin-mineral premix Ovisan® (Sano Company, Croatia) was added into the premix. The goats whose milk was positive on the bacteriological examination were divided into two groups: to one group (number of treated halves, N=20), the composition from Example 11 was applied; while in the other group (N=15), intramammary suspension of amoxicillin with clavulanic acid (Klavuxil®; Genera Company, Croatia) was applied; all by three-times application regimen.

During the testing of tolerability of the composition from Example 11, neither behavioural changes in any goat, nor macroscopical appearance of the udder (edema and redness) and milk, nor udder sensitivity to touch were observed. The milk samples from left and right udder halves were sampled in previously marked sterile plastic tubes after milking of the first few jets. The samples were taken before the first application of the formulation from Example 11, 12 h after the first application, 24 h after the first application, and on 7. day after the first application of the composition. The milk samples were kept at 4° C. until the next day and analysed in the laboratory for mastitis and raw milk quality at the Croatian Veterinary Institute.

The testing of the efficacy of the bacteriological cure was performed according to the directions from European Medicinal Agency (EMA); see literature reference 34. The milk sampling was conducted by the standard methodology, while the microbiological examination was carried out according to standard procedures; see literature reference 35.

The results of bacteriological cure from mastitis in goats are presented in Table 18.

Example 19. A Review of the Successful Wound Healing on the Mare Leg with the Administration of the Composition from the Present Invention from Example 11 in the Form of the Solution The case of wound healing on the front leg of the female horse is described. It was a deep wound in the ergot area of the front leg which arose when the hind leg of the mare gripped the front leg during downhole. Before starting the administration of the composition from Example 11, the wound had been treated conservatively with different preparations unsuccessfully.

The wound was formed during the galloping of the mare, when she "overreached" herself with the hind legs. Then, the cranial part of the hoof and horseshoe of the hind leg injured the knuckle area of the front foot. This caused a wound of elliptical shape with a dimensions of 2×4 cm. The mare exhibited signs of lameness immediately after the injury, scored as 4/5 (American Association Equine Practitioners). Immediately after the injury, the wound was shaved and flushed with ordinary cold water and after that, treated with iodine (povidone-iodine, 0.01%) and sprayed with silver nitrate spray. The wound was closed to avoid infectious contamination. Since the mare was already vaccinated against tetanus, the TAT serum was not applied. The mare was allowed to rest for two weeks and the wound was treated on a daily basis by mechanical cleansing and kept clean and dry. The wound was treated with iodine and silver nitrate spray each 48 h. After 5 days, the wound started to heal and was getting better. Then, the wound was started to be treated with zinc-vitamin ointment. After two weeks, the mare was introduced back to work. However, the wound started bleeding as soon as the mare started galloping. The wound was disinfected again with iodine and a topical antibiotic based on cephalosporin in the formulation for intramammary application was applied (Cobactan®). Together with the mechanical wound cleansing, the wound was locally treated with an antibiotic for a further 5 days. Then, further work with the mare was tried, but the wound started to bleed again.

After that, the wound was washed with physiological solution, dried, and treated with the composition form the Example 11, once a day, during 5 days. The improvement visible through epithelization could be observed after 48 h, while the complete healing occurred after 96 h. The mare was limping only during first few days, but afterwards no signs of lameness were observed. The recovery was complete.

CONCLUSION

Experimental results showed that the specific mixture of liquid polyethylene glycols (PEG) like PEG 400 in combination with lecithins in amount from 0.1-3.5% mass of the extraction solvent (ES), in an unexpected manner, effectively and chemoselectively extracts active propolis substances p-coumaric acid (1), trans-ferulic acid (2), caffeic acid (3) and 2-phenethyl 3,4-dihydroxy-trans-cinnamate (4), in comparison to pure solvents like 96% ethanol, PEG 400 or mixtures of EtOH and the same lecithins.

The exact quantitative composition of the key active substances 1-4 and accompanying ingredients 5-10 in the primary liquid propolis extract is determined by the use of a suitable analytical HPLC method developed in this invention. Then, such a primary extract is standardized with the same extraction solvent (ES) which was employed in the extraction step. This results in a liquid propolis extract according to this invention, with known and standardized concentrations of the key active substances 1-4. Thus prepared standardized propolis extract is used as an active pharmaceutical ingredient (API), active cosmetic ingredient (ACI), or food ingredient for manufacturing of functional food products and food supplements.

The composition from the present invention based on the said liquid propolis extract, which contains the key active substances p-coumaric acid (1; 10-1,300 μg/g), trans-ferulic acid (2; 10-800 μg/g), caffeic acid (3; 5-300 μg/g), and 2-phenethyl 3,4-dihydroxy-trans-cinnamate (4; 5-400 μg/g) is an effective agent in the therapy of inflammatory diseases, bacterial infections, fungal infections, viral diseases, autoimmune diseases, functional gastrointestinal disorders, for mucosa regeneration, treatment of burns and wound healing, and for treatment of cancer diseases.

INDUSTRIAL APPLICABILITY

Due to the wide practical use of the liquid propolis extract and the pharmaceutical composition on its basis, the industrial applicability of the present invention is obvious.

The invention claimed is:

1. A standardized liquid propolis extract, wherein the liquid propolis extract consists of:
    0.1-10.0% w/w dry propolis extract dissolved in 90.0-99.9% w/w extraction solvent;
    wherein the dry propolis extract comprises two or more of p-coumaric acid, trans-ferulic acid, caffeic acid, and 2-phenylethyl 3,4-dihydroxy-trans-cinnamate (CAPE); and
    wherein the extraction solvent consists of:
        (a) 96.5-99.9% w/w of one or more liquid polyethylene glycols (PEG) 200-600; and
        (b) 0.1-3.5% w/w lecithin or hydrolysed lecithin; and
    wherein quantitative contents of the two or more of p-coumaric acid, trans-ferulic acid, caffeic acid, and CAPE in the standardized liquid propolis extract are selected from the group consisting of:
        (i) 100-1,300 μg/mL p-coumaric acid;
        (ii) 75-800 μg/mL trans-ferulic acid;
        (iii) 25-300 μg/mL caffeic acid; and
        (iv) 40-400 μg/mL CAPE.

2. The standardized liquid propolis extract of claim 1, wherein the liquid polyethylene glycol (PEG) is selected from the group consisting of: polyethylene glycol 200, polyethylene glycol 300, polyethylene glycol 400, and polyethylene glycol 600, or mixtures thereof.

3. The standardized liquid propolis extract of claim 1, wherein the lecithin or hydrolysed lecithin is characterized by hydrophilic-lipophilic balance (HLB) factor from 2-12, and is selected from the group consisting of: soybean lecithin (*Glycine max* L); sunflower lecithin (*Helianthus annuus* L); rapeseed lecithin (*Brassica napus* L); canola lecithin (*Brassica rapa* L); lecithin from chicken (*Gallus gallus domesticus* L) eggs; deoiled products of said lecithins; hydrogenated lecithins from soybean, sunflower, rapeseed, canola, or chicken eggs; hydrolysed lecithins from soybean, sunflower, rapeseed, canola, or chicken eggs; and enzyme-modified derivatives of said lecithins; or mixtures thereof.

4. The standardized liquid propolis extract of claim 1, wherein the extraction solvent consists of:
    (i) 97-99% w/w polyethylene glycol (PEG) 200, polyethylene glycol 300, polyethylene glycol 400, or mixtures thereof; and
    (ii) 1-3% w/w native lecithin, deoleinized lecithin, or hydrolysed lecithin from soybean (*Glycine max* L), sunflower (*Helianthus annuus* L), rapeseed (*Brassica napus* L), canola (*Brassica rapa* L), or mixtures thereof.

5. The standardized liquid propolis extract of claim 1, wherein:
    the quantitative contents of the two or more of p-coumaric acid, trans-ferulic acid, caffeic acid, and CAPE in the standardized liquid propolis extract are selected from the group consisting of:
        (i) 500-1,300 μg/mL p-coumaric acid;
        (ii) 300-800 μg/mL trans-ferulic acid;
        (iii) 100-300 μg/mL caffeic acid; and
        (iv) 100-400 μg/mL CAPE.

6. A process for production of the standardized liquid propolis extract of claim 1, the process comprising:
    (a) cooling a crude propolis at −20° C. for at least 1 h to form a chilled propolis;
    (b) milling the chilled propolis with sieving through 1-8 mm pores to form a milled propolis;
    (c) extracting the milled propolis with the extraction solvent wherein the extracting comprises:
        incubating the milled propolis with the extraction solvent at 10-150° C. for 5 minutes to 72 hours to form an extracted propolis solution, wherein the extraction solvent comprises 96.5-99.9% w/w of one or more liquid polyethylene glycols (PEG) 200-600 and 0.1-3.5% w/w lecithin or hydrolysed lecithin;
    (d) filtering the extracted propolis solution through a series of filters with pores from 100 μm to 5 μm to generate a liquid propolis extract, wherein the ratio of the weight of the crude propolis to the weight of the liquid propolis extract is 1:2 to 1:20;

(e) analyzing the amount of p-coumaric acid, trans-ferulic acid, caffeic acid, and CAPE using high performance liquid chromatography; and (f) adding fresh extraction solvent to the liquid propolis extract to provide for quantitative contents of the two or more of p-coumaric acid, trans-ferulic acid, caffeic acid, and CAPE selected from the group consisting of:
(i) 100-1,300 µg/mL p-coumaric acid;
(ii) 75-800 µg/mL trans-ferulic acid;
(iii) 25-300 µg/mL caffeic acid; and
(iv) 40-400 µg/mL CAPE.

7. The standardized liquid propolis extract of claim 1, wherein the standardized liquid propolis extract is an ingredient in a pharmaceutical product, a cosmetic product, an agrochemical product, or a food product.

8. A pharmaceutical composition consisting of:
(I) from 5-95% w/w of the standardized liquid propolis extract of claim 1; and
(II) one or more pharmaceutical excipients required for final dosage form preparation selected from the group consisting of: solution, suspension, gel, cream, ointment, and spray for oral or nasal application;
wherein the composition is characterized by quantitative contents of the two or more of p-coumaric acid, trans-ferulic acid, caffeic acid, and CAPE in the standardized liquid propolis extract are selected from the group consisting of:
(i) 10-1,300 µg/g p-coumaric acid;
(ii) 10-800 µg/g trans-ferulic acid;
(iii) 5-300 µg/g caffeic acid; and
(iv) 5-400 µg/g CAPE.

9. The liquid propolis extract of claim 1, wherein the extraction solvent comprises 97% PEG400 and 3% soy lecithin.

10. The liquid propolis extract of claim 1, wherein the dry propolis extract is made by the process of:
(a) cooling a crude propolis at −20° C. for at least 1 h to form a chilled propolis;
(b) milling the chilled propolis with sieving through 1-8 mm pores to form a milled propolis;
(c) extracting the milled propolis with the extraction solvent wherein the extracting comprises: incubating the milled propolis with the extraction solvent at 10-150° C. for 5 minutes to 72 hours to form an extracted propolis solution;
(d) filtering the extracted propolis solution through a series of filters with pores from 100 µm to 5 µm to generate a liquid propolis extract, wherein the weight ratio of crude propolis to the weight of the liquid propolis extract is 1:2 to 1:20; and
(e) drying the liquid propolis extract to form the dry propolis extract.

11. The liquid propolis extract of claim 10, wherein the weight ratio of crude propolis to the weight of the liquid propolis extract is 1:3 to 1:5.

12. The liquid propolis extract of claim 10, wherein the extraction solvent comprises 97% PEG400 and 3% soy lecithin.

* * * * *

UNITED STATES PATENT AND TRADEMARK OFFICE
CERTIFICATE OF CORRECTION

PATENT NO. : 12,350,296 B2  
APPLICATION NO. : 17/430567  
DATED : July 8, 2025  
INVENTOR(S) : Sasa Radic et al.

Page 1 of 1

It is certified that error appears in the above-identified patent and that said Letters Patent is hereby corrected as shown below:

In the Claims

In Column 44, Line 34, Claim 4, delete "deoleinized lecithin" and insert -- deoiled lecithin --, therefor.
In Column 46, Line 1, Claim 9, delete "liquid" and insert -- standardized liquid --, therefor.
In Column 46, Line 4, Claim 10, delete "liquid" and insert -- standardized liquid --, therefor.
In Column 46, Line 24, Claim 11, delete "liquid" and insert -- standardized liquid --, therefor.
In Column 46, Line 27, Claim 12, delete "liquid" and insert -- standardized liquid --, therefor.

Signed and Sealed this  
Twenty-third Day of December, 2025

John A. Squires  
*Director of the United States Patent and Trademark Office*